(12) United States Patent
Skinner

(10) Patent No.: US 12,384,830 B2
(45) Date of Patent: Aug. 12, 2025

(54) COMPOSITIONS AND METHODS FOR IMPROVING IMMUNOTHERAPY

(71) Applicant: Regents of the University of Minnesota, Minneapolis, MN (US)

(72) Inventor: Pamela J. Skinner, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 734 days.

(21) Appl. No.: 15/996,337

(22) Filed: Jun. 1, 2018

(65) Prior Publication Data

US 2018/0371057 A1    Dec. 27, 2018

Related U.S. Application Data

(60) Provisional application No. 62/514,438, filed on Jun. 2, 2017.

(51) Int. Cl.
| | |
|---|---|
| C07K 14/715 | (2006.01) |
| A61K 40/11 | (2025.01) |
| A61K 40/30 | (2025.01) |
| A61K 40/31 | (2025.01) |
| A61K 40/46 | (2025.01) |
| A61P 31/18 | (2006.01) |
| C07K 14/705 | (2006.01) |
| C07K 14/725 | (2006.01) |
| C12N 7/00 | (2006.01) |
| G01N 33/569 | (2006.01) |

(52) U.S. Cl.
CPC .......... *C07K 14/7158* (2013.01); *A61K 40/11* (2025.01); *A61K 40/30* (2025.01); *A61K 40/31* (2025.01); *A61K 40/46* (2025.01); *A61P 31/18* (2018.01); *C07K 14/7051* (2013.01); *C07K 14/70521* (2013.01); *C12N 7/00* (2013.01); *G01N 33/56983* (2013.01); *C07K 2319/03* (2013.01); *C07K 2319/20* (2013.01); *C12N 2740/13043* (2013.01); *C12N 2740/16043* (2013.01); *G01N 2800/26* (2013.01); *G01N 2800/52* (2013.01)

(58) Field of Classification Search
CPC .............. C07K 14/158; C07K 14/7158; C07K 14/7051; C07K 14/70521; C07K 2319/03; C07K 2319/20; A61K 35/17; A61K 2039/5156; A61K 2039/5158; A61K 39/0011; A61P 31/18; C12N 7/00; C12N 2740/13043; C12N 2740/16043; G01N 33/56983; G01N 2800/26; G01N 2800/52
See application file for complete search history.

(56) References Cited

U.S. PATENT DOCUMENTS

| | | |
|---|---|---|
| 7,115,262 B1 | 10/2006 | Berger et al. |
| 7,151,087 B2 | 12/2006 | Combadiere et al. |
| 8,338,448 B2 | 12/2012 | Clark et al. |
| 8,420,099 B2 | 4/2013 | Berger et al. |
| 9,629,877 B2 | 4/2017 | Cooper et al. |
| 9,707,257 B2 | 7/2017 | Fraser, Jr. |
| 10,094,827 B2 | 10/2018 | Vinnik et al. |
| 10,233,464 B2 | 3/2019 | Pauza et al. |
| 10,294,299 B2 | 5/2019 | Pantaleo et al. |
| 10,323,289 B2 | 6/2019 | Huot et al. |
| 2011/0250165 A1 | 10/2011 | Marasco et al. |
| 2012/0213783 A1 | 8/2012 | Rosenberg et al. |
| 2013/0189264 A1 | 7/2013 | Berger et al. |
| 2016/0175358 A1* | 6/2016 | Jakobovits ............. A61K 35/17 424/93.2 |
| 2017/0267739 A1 | 9/2017 | Berger et al. |
| 2018/0080008 A1 | 3/2018 | Liang et al. |
| 2018/0169108 A1 | 6/2018 | Laird et al. |
| 2018/0201901 A1* | 7/2018 | Duchateau ............. A61K 35/17 |
| 2019/0194326 A1 | 6/2019 | Wang |
| 2019/0241633 A1* | 8/2019 | Fotin-Mleczek .... A61K 48/005 |

FOREIGN PATENT DOCUMENTS

| | | |
|---|---|---|
| WO | WO 2012/079000 | 6/2012 |
| WO | WO 2013/059593 | 4/2013 |
| WO | WO 2015/077789 | 5/2015 |
| WO | WO 2016/025454 | 2/2016 |

OTHER PUBLICATIONS

Hodges et al. "Diagnostic role of tests for T cell receptor (TCR) genes." Journal of clinical pathology 56.1 (2003): 1-11 (Year: 2003).*
He et al. "Follicular CXCR5-expressing CD8+ T cells curtail chronic viral infection." Nature 537.7620 (2016): 412-416 (Year: 2016).*
Tumaini et al. "Simplified process for the production of anti-CD19-CAR-engineered T cells." Cytotherapy 15.11 (2013): 1406-1415 (Year: 2013).*
Bleul et al., "A highly efficacious lymphocyte chemoattractant, stromal cell-derived factor 1 (SDF-1)," J. Exp. Med., 184(3):1101-9, Sep. 1996.
Brentjens et al., "Treatment of chronic lymphocytic leukemia with genetically targeted autologous T cells: case report of an unforeseen adverse event in a phase I clinical trial," Mol. Ther., 18(4):666-8, Apr. 2010.
Bronnimann et al., "The B-cell follicle in HIV infection: Barrier to a cure," Frontiers in immunology, 9:20, Jan. 2018.
Chinnasamy et al., "Multicistronic lentiviral vectors containing the FMDV 2A cleavage factor demonstrate robust expression of encoded genes at limiting MOI," Virol. J., 3:14, Mar. 2006.

(Continued)

*Primary Examiner* — Fereydoun G Sajjadi
*Assistant Examiner* — Alexander W Nicol
(74) *Attorney, Agent, or Firm* — Fish & Richardson P.C.

(57) ABSTRACT

This disclosure provides compositions and methods for improving immunotherapy, specifically against diseases like HIV or lymphoma that manifest within B cell follicles.

11 Claims, 15 Drawing Sheets

Specification includes a Sequence Listing.

(56) References Cited

OTHER PUBLICATIONS

Connick et al., "Compartmentalization of SIV Replication Within Secondary Lymphoid Tissues of Rhesus Macaques is Linked to Disease Stage and Inversely Related to Localization of Virus-Specific CTL," Journal of immunology, 193(11):5613-5625, Dec. 2014.
Connick et al., "CTL fail to accumulate at sites of HIV-1 replication in lymphoid tissue," J. Immunol., 178(11):6975-83, Jun. 2007.
Delang et al., "The viral capping enzyme nsP1: a novel target for the inhibition of chikungunya virus infection," Sci. Rep., 6:31819, Aug. 2016.
Dzhagalov et al., "Elimination of self-reactive T cells in the thymus: a timeline for negative selection," PLoS Biol., 11(5):e1001566, May 2013.
Eyquem et al., "Targeting a CAR to the TRAC locus with CRISPR/Cas9 enhances tumour rejection," Nature, 543(7643):113-7, Mar. 2017.
GenBank Accession No. NM_001716.4, "Homo sapiens chemokine (C-X-C motif) receptor 5 (CXCR5), transcript variant 1, mRNA," Mar. 15, 2015, 4 pages.
GenBank Accession No. NM_032966.2, "*Homo sapiens* chemokine (C-X-C motif) receptor 5 (CXCR5), transcript variant 2, mRNA," Dec. 30, 2015, 4 pages.
GenBank Accession No. NP_001707.1, "C-X-C chemokine receptor type 5 isoform 1 [*Homo sapiens*]," Mar. 15, 2015, 3 pages.
GenBank Accession No. NP_116743.1, "C-X-C chemokine receptor type 5 isoform 2 [*Homo sapiens*]," Dec. 30, 2015, 3 pages.
GenBank Accession No. XP_001100017.1, "Predicted: C-X-C chemokine receptor type 5 isoform X1 [Macaca mulatta]," Dec. 21, 2015, 1 page.
Ghanem et al., "Bispecific chimeric antigen receptors targeting the CD4 binding site and high-mannose Glycans of gp120 optimized for anti-human immunodeficiency virus potency and breadth with minimal immunogenicity," Cytotherapy, 20(3):407-19, Mar. 2018.
Gori et al., "Protection of mice from methotrexate toxicity by ex vivo transduction using lentivirus vectors expressing drug-resistant dihydrofolate reductase," J. Pharmacol. Exp. Ther., 322(3):989-97, Sep. 2007.
Grupp et al., "Chimeric antigen receptor-modified T cells for acute lymphoid leukemia," N. Engl. J. Med., 368(16):1509-18, Apr. 2013.
Hale et al., "Engineering HIV-Resistant, Anti-HIV Chimeric Antigen Receptor T Cells," Mol. Ther., 25(3):570-9, Mar. 2017.
Han et al., "Chimeric antigen receptor-engineered T cells for cancer immunotherapy: progress and challenges," J. Hematol. Oncol., 6:47, Jul. 2013.
Haran et al., "Simian Immunodeficiency Virus (SIV)-Specific Chimeric Antigen Receptor-T Cells Engineered to Target B Cell Follicles and Suppress SIV Replication," Front Immunol., 9:492, Mar. 2018.
Haso et al., "Anti-CD22-chimeric antigen receptors targeting B-cell precursor acute lymphoblastic leukemia," Blood, 121(7):1165-74, Feb. 2013.
Hughes et al., "Transfer of a TCR gene derived from a patient with a marked antitumor response conveys highly active T-cell effector functions," Hum. Gene Ther., 16(4):457-72, Apr. 2005.
Ibrahimi et al., "Highly efficient multicistronic lentiviral vectors with peptide 2A sequences," Hum. Gene Ther., 20(8):845-60, Aug. 2009.
Kim et al., "High cleavage efficiency of a 2A peptide derived from porcine teschovirus-1 in human cell lines, zebrafish and mice," PLoS One, 6(4):e18556, 2011.
Li et al., "Simian immunodeficiency virus-producing cells in follicles are partially suppressed by CD8+ cells in vivo," J. Virol., 90(24):11168-11180, Dec. 2016.
Liu et al., "Novel CD4-Based Bispecific Chimeric Antigen Receptor Designed for Enhanced Anti-HIV Potency and Absence of HIV Entry Receptor Activity," J. Virology, 89(13):6685-94, Jul. 2015.

Meditz et al., "SDF-1alpha is a potent inducer of HIV-1-Specific CD8+ T-cell chemotaxis, but migration of CD8+ T cells is impaired at high viral loads," AIDS Res. Hum. Retrovir., 24(7):977-85, Jul. 2008.
Melichar et al., "Distinct temporal patterns of T cell receptor signaling during positive versus negative selection in situ," Sci. Signal, 6(297):ra92, Oct. 2013.
Miles et al., "Follicular regulatory CD8 T cells impair the germinal center response in SIV and ex vivo HIV infection," PLoS pathogens, 12(10):e1005924, Oct. 2016.
Miles et al., "Follicular regulatory T cells impair follicular T helper cells in HIV and SIV infection," Nature Communications, 6(8608), Oct. 2015.
Mizuguchi et al., "IRES-dependent second gene expression is significantly lower than cap-dependent first gene expression in a bicistronic vector," Mol. Ther., 1(4):376-82, Apr. 2000.
Morgan et al., "Recognition of glioma stem cells by genetically modified T cells targeting EGFRvIII and development of adoptive cell therapy for glioma," Hum. Gene Ther., 23(10):1043-53, Jul. 2012.
Park et al., "Treating cancer with genetically engineered T cells," Trends Biotechnol., 29(11):550-7, Nov. 2011.
Porter et al., "Comparison of efficiency of infection of human gene therapy target cells via four different retroviral receptors," Hum. Gene Ther., 7(8):913-9, May 1996.
Sallusto et al., "Central memory and effector memory T cell subsets: function, generation, and maintenance," Annu. Rev. Immunol., 22:745-63, 2004.
Skinner and Connick, "Overcoming the Immune Privilege of B cell Follicles to Cure HIV-1 Infection," Journal of Human Virology & Retrovirology, 1(1):00001, Apr. 2014.
Till et al., "Adoptive immunotherapy for indolent non-Hodgkin lymphoma and mantle cell lymphoma using genetically modified autologous CD20-specific T cells," Blood, 12(6):2261-71, Sep. 2008.
Tumaini et al., "Simplified process for the production of anti-CD19-CAR- engineered T cells," Cytotherapy, 15(11):1406-15, Nov. 2013.
Vagner et al., "Irresistible IRES. Attracting the translation machinery to internal ribosome entry sites," EMBO Reports, 2(10):893-8, Oct. 2001.
Webb et al., "The human IL-15 superagonist ALT-803 directs SIV-specific CD8+ T cells into B-cell follicles," Blood Advances, 2(2):76-84, Jan. 2018.
Wodarz et al., "Virus and CTL dynamics in the extra-follicular and follicular tissue compartments in SIV-infected macaques," PLOS computational biology, 14(10):e1006461, Oct. 2018.
Younan et al., "Positive selection of mC46-expressing CD4+ T cells and maintenance of virus specific immunity in a primate AIDS model," Blood, 122(2):179-87, Jul. 2013.
Zhen et al., "HIV-specific Immunity Derived From Chimeric Antigen Receptor-engineered Stem Cells," Mol. Ther., 23(8):1358-67, Aug. 2015.
Bronnimann et al., "The B-Cell Follicle in HIV Infection: Barrier to a Cure," Front. Immunol., 9:20, Jan. 25, 2018, 13 pages.
Ayala et al., "CXCR5-Dependent Entry of CD8 T Cells into Rhesus Macaque B-Cell Follicles Achieved through T-Cell Engineering," J. Virology, 91(11):e02507-16, Jun. 2017, 17 pages.
ClinicalTrials.gov [online], "Comparison of Dendritic Cell-Based Therapeutic Vaccine Strategies for HIV Functional Cure (DC-HIV04)," NCT03758625, last updated Jun. 12, 2020, retrieved on Dec. 11, 2020, retrieved from URL<https://clinicaltrials.gov/ct2/show/NCT03758625>, 22 pages.
ClinicalTrials.gov [online], "CD4 CAR+ ZFN-modified T Cells in HIV Therapy," NCT03617198, last updated Oct. 8, 2020, retrieved on Dec. 11, 2020, retrieved from URL<https://clinicaltrials.gov/ct2/show/study/NCT03617198>, 16 pages.
ClinicalTrials.gov [online], "Chidamide in Combination With ART for Reactivation of the Latent HIV-1 Reservoir," NCT02902185; last updated Apr. 26, 2018, retrieved on Dec. 14, 2020, retrieved from URL<https://clinicaltrials.gov/ct2/show/NCT02902185>, 16 pages.
ClinicalTrials.gov [online], "Combination Therapy With 3BNC117 and 10-1074 in HIV-Infected Individuals," NCT03571204, last

(56) References Cited

OTHER PUBLICATIONS updated Apr. 27, 2020, retrieved on Dec. 14, 2020, retrieved from URL<https://clinicaltrials.gov/ct2/show/NCT03571204>, 24 pages.
ClinicalTrials.gov [online], "Combination Therapy With VRC-HIVMAB060-00-AB (VRC01) and 10-1074 in HIV-Infected Individuals Undergoing Sequential Treatment Interruptions," NCT03831945, last updated Dec. 11, 2020, retrieved on Dec. 14, 2020, retrieved from URL<https://clinicaltrials.gov/ct2/show/NCT03831945>, 22 pages.
ClinicalTrials.gov [online], "Combining TLR9 Agonist With bNAbs for Reservoir Reduction and Immunological Control of HIV (TITAN)," NCT03837756, last updated May 7, 2019, retrieved on Dec. 14, 2020, retrieved from URL:https://clinicaltrials.gov/ct2/show/NCT03837756>, 18 pages.
ClinicalTrials.gov [online], "Early cART and cART in Combination With Autologous HIV-1 Specific Cytotoxic T Lymphocyte (CTL) Infusion in The Treatment of Acute HIV-1 Infected Adults," NCT02231281, last updated Apr. 26, 2018, retrieved on Dec. 11, 2020, retrieved from URL<https://clinicaltrials.gov/ct2/show/results/NCT02231281>, 17 pages.
ClinicalTrials.gov [online], "Effect of Chidamide Combined With CAT-T or TCR-T Cell Therapy on HIV-1 Latent Reservoir," NCT03980691, last updated Jun. 10, 2019, retrieved on Dec. 14, 2020, retrieved from URL<https://clinicaltrials.gov/ct2/show/NCT03980691>, 16 pages.
ClinicalTrials.gov [online], "Evaluating a Combination of Immune-based Therapies to Achieve a Remission of HIV Infection (HIVACAR)," NCT03619278, last updated Mar. 31, 2020, retrieved on Dec. 14, 2020, retrieved from URL<https://clinicaltrials.gov/et2/show/NCT03619278>, 18 pages.
ClinicalTrials.gov [online], "Evaluating the Safety and Efficacy of Romidepsin in Combination With Antiretroviral Therapy in HIV-Infected Adults With Suppressed Viral Load," NCT01933594, last updated May 23, 2019, retrieved on Dec. 14, 2020, retrieved from URL<https://clinicaltrials.gov/ct2/show/NCT01933594>, 111 pages.
ClinicalTrials.gov [online], "Functional Cure Study of HIV-infected Patients," NCT02794545, last updated Mar. 13, 2018, retrieved on Dec. 14, 2020, retrieved from URL<https://clinicaltrials.gov/ct2/show/NCT02794545>, 13 pages.
ClinicalTrials.gov [online], "HIV Eradication Through Cord-blood Transplantation (HIVECT)," NCT02923076, last updated Nov. 1, 2016, retrieved on Dec. 14, 2020, retrieved from URL<https://clinicaltrials.gov/ct2/show/NCT02923076>, 13 pages.
ClinicalTrials.gov [online], "HIV-1 Specific T-Cells (HST-NEETs) for HIV-Infected Individuals (RESIST)," NCT03485963, last updated Jul. 14, 2020, retrieved on Dec. 11, 2020, retrieved from URL<https://clinicaltrials.gov/ct2/show/study/NCT03485963>, 16 pages.
ClinicalTrials.gov [online], "Iimmunogenicity Study of Vacc-4x Versus Placebo in Patients Infected With HIV," NCT00659789, last updated Feb. 23, 2017, retrieved on Dec. 14, 2020, retrieved from URL<https://www.clinicaltrials.gov/ct2/show/NCT00659789>, 30 pages.
ClinicalTrials.gov [online], "Impact of Recombinant Human Growth Hormone on HIV Persistence," NCT03091374, last updated Sep. 18, 2019, retrieved on Dec. 14, 2020, retrieved from URL<https://clinicaltrials.gov/ct2/show/NCT03091374>, 20 pages.
ClinicalTrials.gov [online], "Lipopeptide Immunisation With GTU-multiHIV Trial," NCT01492985, last updated Jul. 5, 2019, retrieved on Dec. 14, 2020, retrieved from URL<https://clinicaltrials.gov/ct2/show/NCT01492985>, 18 pages.
ClinicalTrials.gov [online], "LRAs United as a Novel Anti-HIV Strategy. (LUNA)" NCT03525730, last updated May 16, 2018, retrieved on Dec. 14, 2020, retrieved from URL<https://clinicaltrials.gov/et2/show/NCT03525730>, 22 pages.
ClinicalTrials.gov [online], "MMF for HIV Reservoir Reduction," NCT03262441, last updated Dec. 3, 2020, retrieved on Dec. 14, 2020, retrieved from URL<https://clinicaltrials.gov/ct2/show/NCT03262441>, 28 pages.
ClinicalTrials.gov [online], "Peg-Interferon Alpha. 2b Combined With Two Intravenous Broadly HIV-I Neutralizing Antibodies 3BNC117 and 10-1074 (BEAT-2) (BEAT-2)," NCT03588715, last updated Jun. 19, 2020, retrieved on Dec. 14, 2020, retrieved from URL<https://clinicaltrials.gov/ct2/show/NCT03588715>, 27 pages.
ClinicalTrials.gov [online], "Reconstitution of HIV-specific Immunity Against HIV," NCT02563509, last updated Jun. 6, 2019, retrieved on Dec. 11, 2020, retrieved from URL<https://clinicaltrials.gov/ct2/show/NCT02563509>, 17 pages.
ClinicalTrials.gov [online], "Reducing Proviral HIV DNA With Interferon-a (BEAT-HIV)," NCT02227277, last updated Apr. 5, 2018, retrieved on Dec. 14, 2020, retrieved from URL<https://clinicaltrials.gov/ct2/show/NCT02227277>, 21 pages.
ClinicalTrials.gov [online], "Reducing the Residual Reservoir of HIV-1 Infected Cells in Patients. Receiving Antiretroviral Therapy (ACTIVATE)," NCT02471430, last updated Feb. 19, 2020, retrieved on Dec. 14, 2020, retrieved from URL<https://clinicaltrials.gov/ct2/show/NCT02471430>, 20 pages.
ClinicalTrials.gov [online], "Research In Viral Eradication of HIV Reservoirs (RIVER)," NCT02336074, last updated Mar. 17, 2020, retrieved on Dec. 14, 2020, retrieved from URL<https://clinicaltrials.gov/ct2/show/NCT02336074>, 51 pages.
ClinicalTrials.gov [online], "Safety and Effect on HIV Transcription of Vorinostat in Patients Receiving Suppressive Combination Antiretroviral Therapy," NCT01365065, last updated Apr. 25, 2017, retrieved on Dec. 14, 2020, retrieved from URL<https://clinicaltrials.gov/ct2/show/NCT01365065>, 17 pages.
ClinicalTrials.gov [online], "Safety and Efficacy of Romidepsin and the Therapeutic Vaccine Vacc-4x for Reduction of the Latent HIV-I Reservoir (REDUC);" NCT02092116, last updated Mar. 1, 2017, retrieved on Dec. 14, 2020, retrieved from URL<https://clinicaltrials.gov/et2/show/NCT02092116>, 33 pages.
ClinicalTrials.gov [online], "Safety and Immunogenicity Study of DNA.HTI, MVA, HTI and ChAdOx1.HTI in HIV-1-positive Patients(AELIX-002)," NCT03204617, last updated Jul. 31, 2020, retrieved on Dec. 14, 2020, retrieved from URL<https://clinicaltrials.gov/ct2/show/NCT03204617>, 23 pages.
ClinicalTrials.gov [online], "Safety and Immunotherapeutic Activity of an Anti-PD-1 Antibody (Cemiplimab) in HIV-1-infected Participants on Suppressive cART;" NCT03787095, last updated Sep. 9, 2020, retrieved on Dec. 11, 2020, retrieved from URL<https://clinicaltrials.gov/ct2/show/NCT03787095>, 20 pages.
ClinicalTrials.gov [online], "Study to Assess Safety and Activity of Combination Therapy of VRC07-523LS and Vorinostat on HIV-infected Persons," NCT03803605, last updated Aug. 18, 2020, retrieved on Dec. 14, 2020, retrieved from URL:https://clinicaltrials.gov/ct2/show/NCT03803605>, 27 pages.
ClinicalTrials.gov [online], "Study to Evaluate the Safety and Effect of HIVconsv Vaccines in Combination With Histone Deacetylase Inhibitor Romidepsin on the Viral Rebound Kinetic After Treatment Interruption in Early Treated HIV-1 Infected Individuals," NCT02616874, last updated. Jan. 17, 2018, retrieved on Dec. 14, 2020, retrieved from URL<https://clinicaltrials.gov/ct2/show/NCT02616874>, 18 pages.
ClinicalTrials.gov [online], "The Effect of Arsenic Trioxide on Eliminating HIV-1 Reservoir Combined With cART," NCT03980665, last updated Jun. 10, 2019, retrieved on Dec. 14, 2020, retrieved from URL<https://clinicaltrials.gov/ct2/show/NCT03980665>, 20 pages.
ClinicalTrials.gov [online], "The Effect of Chimeric Antigen Receptor (CAR)-T Cell Therapy on the Reconstitution of HIV-specific Immune Function," NCT03240328, last updated Jul. 1, 2020, retrieved on Dec. 11, 2020, retrieved from URL<https://clinicaltrials.gov/ct2/show/NCT03240328>, 19 pages.
ClinicalTrials.gov [online], "The Effect of Ixazomib on the Latent HIV Reservoir," NCT02946047, last updated Oct. 22, 2020, retrieved on Dec. 14, 2020, retrieved from URL<https://clinicaltrials.gov/ct2/show/NCT02946047>, 16 pages.
ClinicalTrials.gov [online], "The HIV Functional Cure Potential of UB-421 in ART Stabilized HIV-1 Patients;" NCT03743376, last updated Nov. 25, 2019, retrieved on Dec. 14, 2020, retrieved from URL<https://clinicaltrials.gov/ct2/show/NCT03743376>, 13 pages.

(56) References Cited

OTHER PUBLICATIONS

ClinicalTrials.gov [online], "Therapeutic Vaccine for HIV," NCT01859325, last updated Mar. 3, 2020, retrieved on Dec. 14, 2020, retrieved from URL<https://clinicaltrials.gov/ct2/show/NCT01859325>, 35 pages.

ClinicalTrials.gov [online], "Toll-like Receptor 9 Agonist Treatment in Chronic HIV-1 Infection (TEACH)," NCT02443935, last updated Jun. 29, 2017, retrieved on Dec. 14, 2020, retrieved from URL<https://clinicaltrials.gov/ct2/show/NCT02443935>, 17 pages.

ClinicalTrials.gov [online], "Vedolizumab Treatment in Antiretroviral Drug Treated Chronic HIV Infection (HAVARTI)," NCT03147859, last updated Jun. 11, 2020, retrieved on Dec. 14, 2020, retrieved from URL<https://clinicaltrials.gov/ct2/show/NCT03147859>, 20 pages.

Rockstroh et al., "Re-boost immunizations with the peptide-based therapeutic HIV vaccine, Vacc-4x, restores geometric mean viral load set-point during treatment interruption," PLoS One, Jan. 30, 2019, 14(1):e0210965, 23 pages.

* cited by examiner

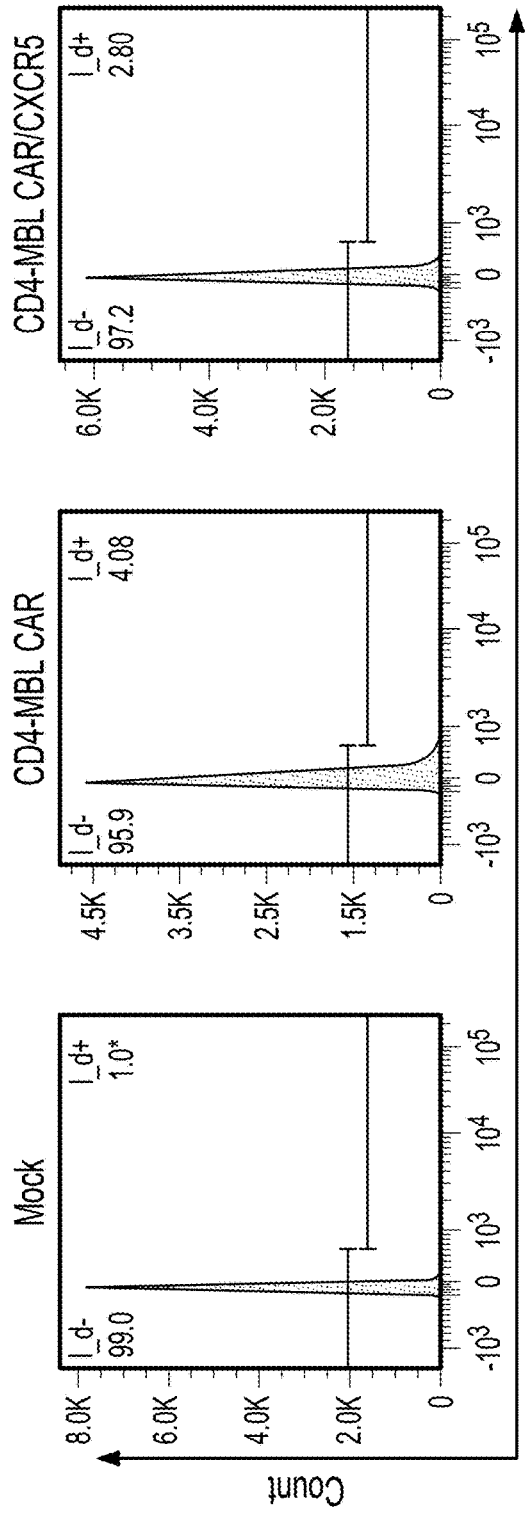
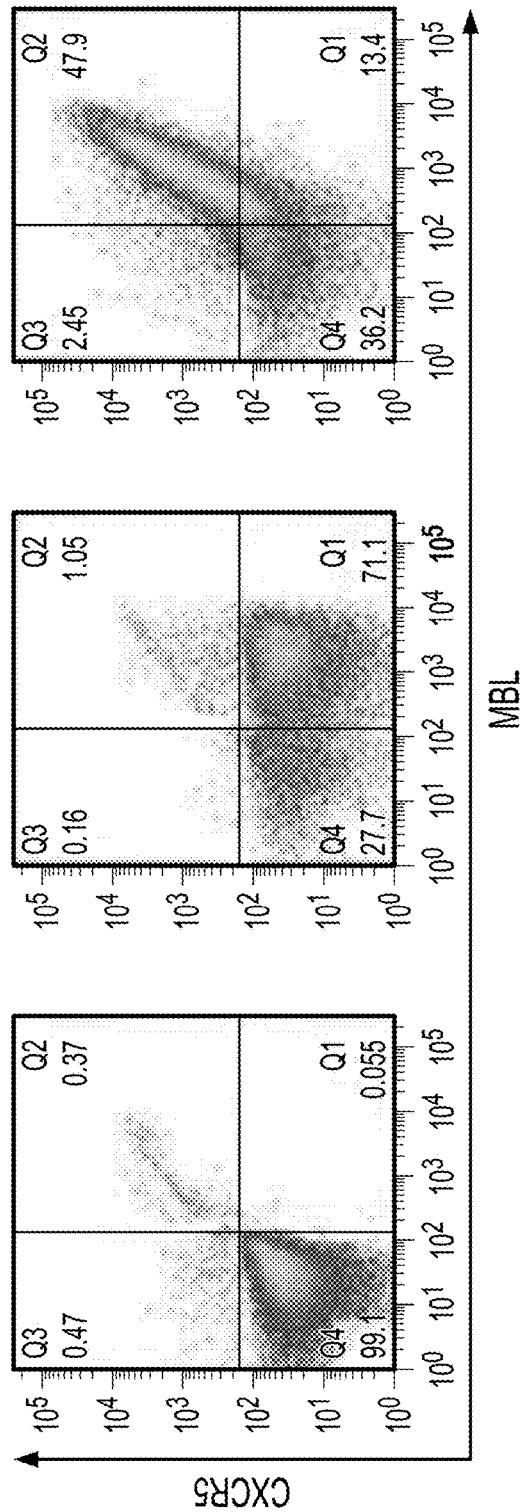
FIG. 2A
FIG. 2B

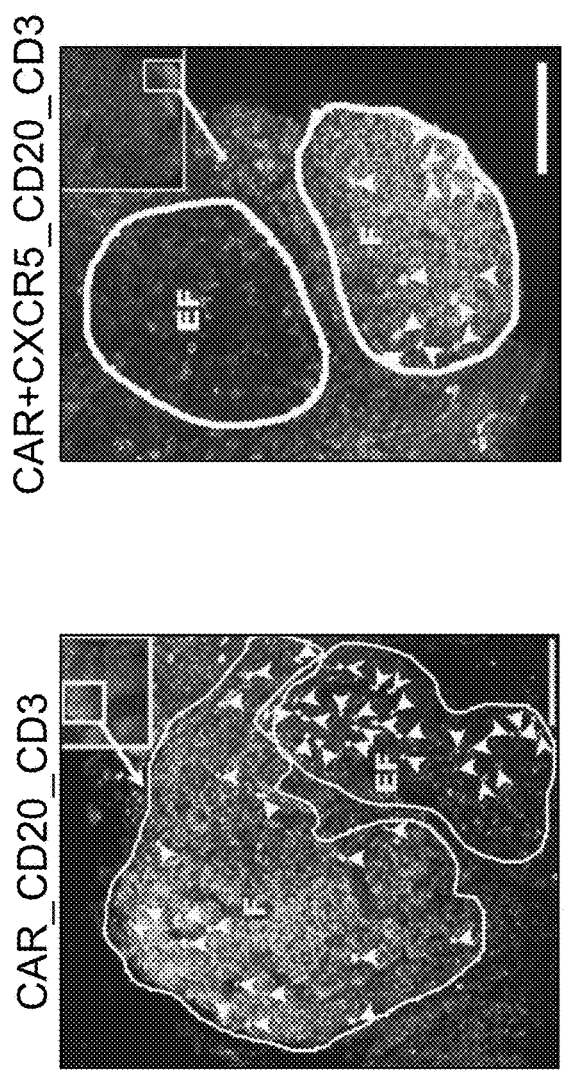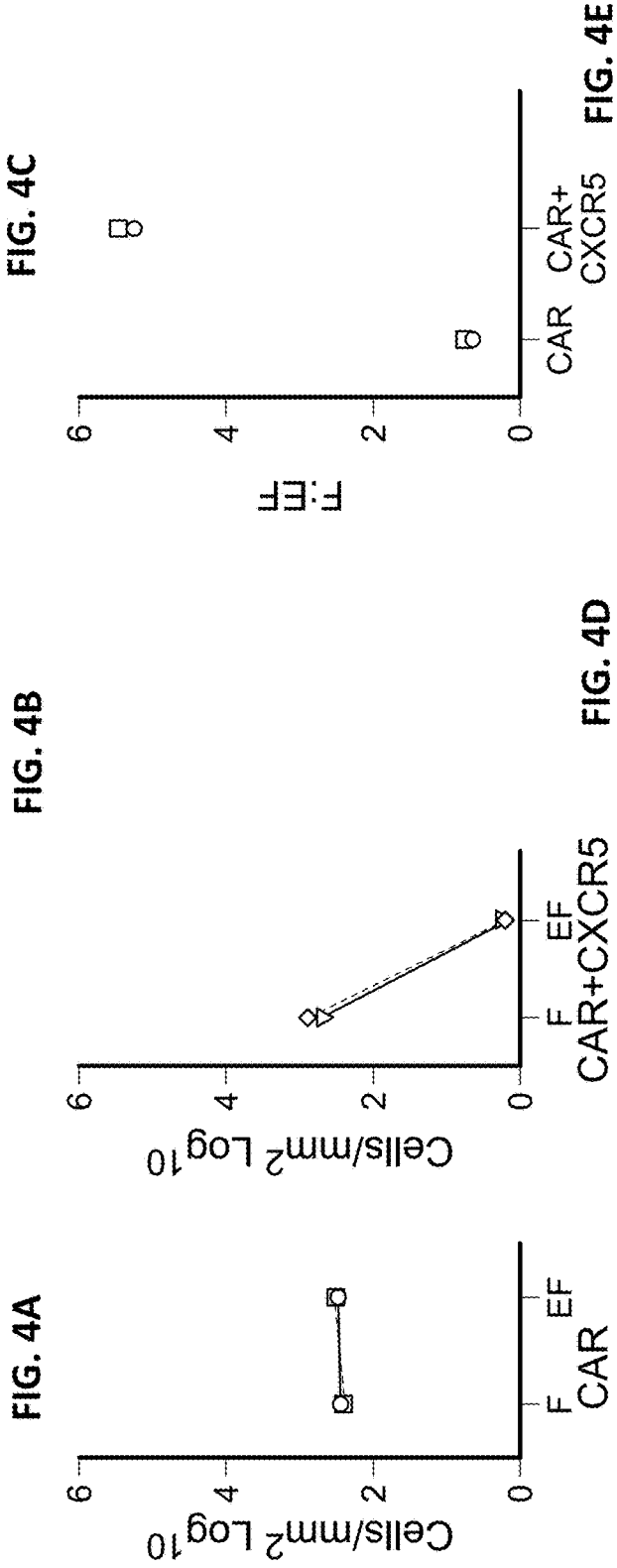

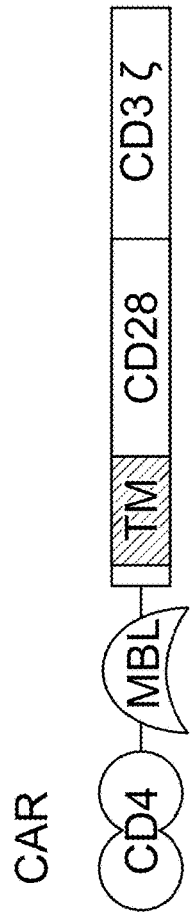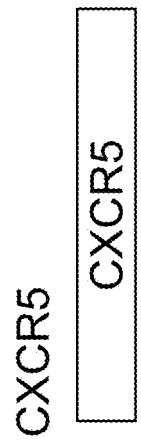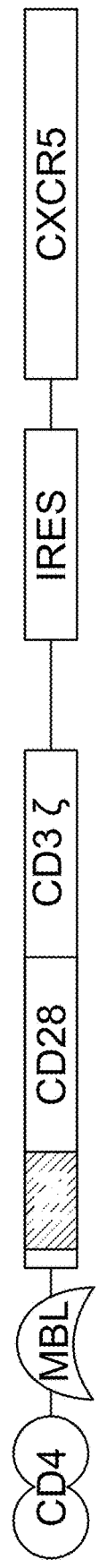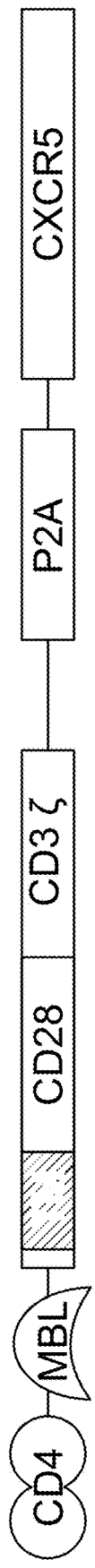
FIG. 5A

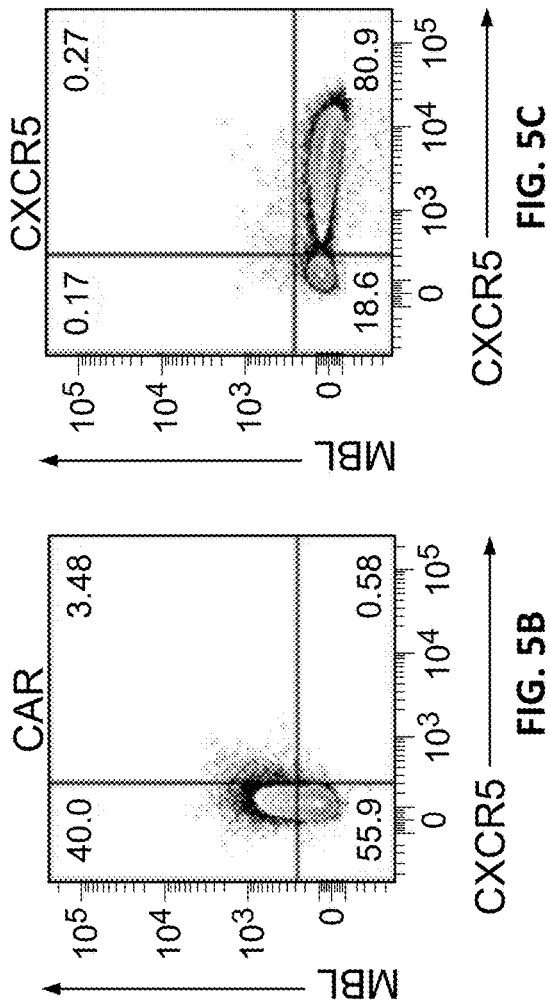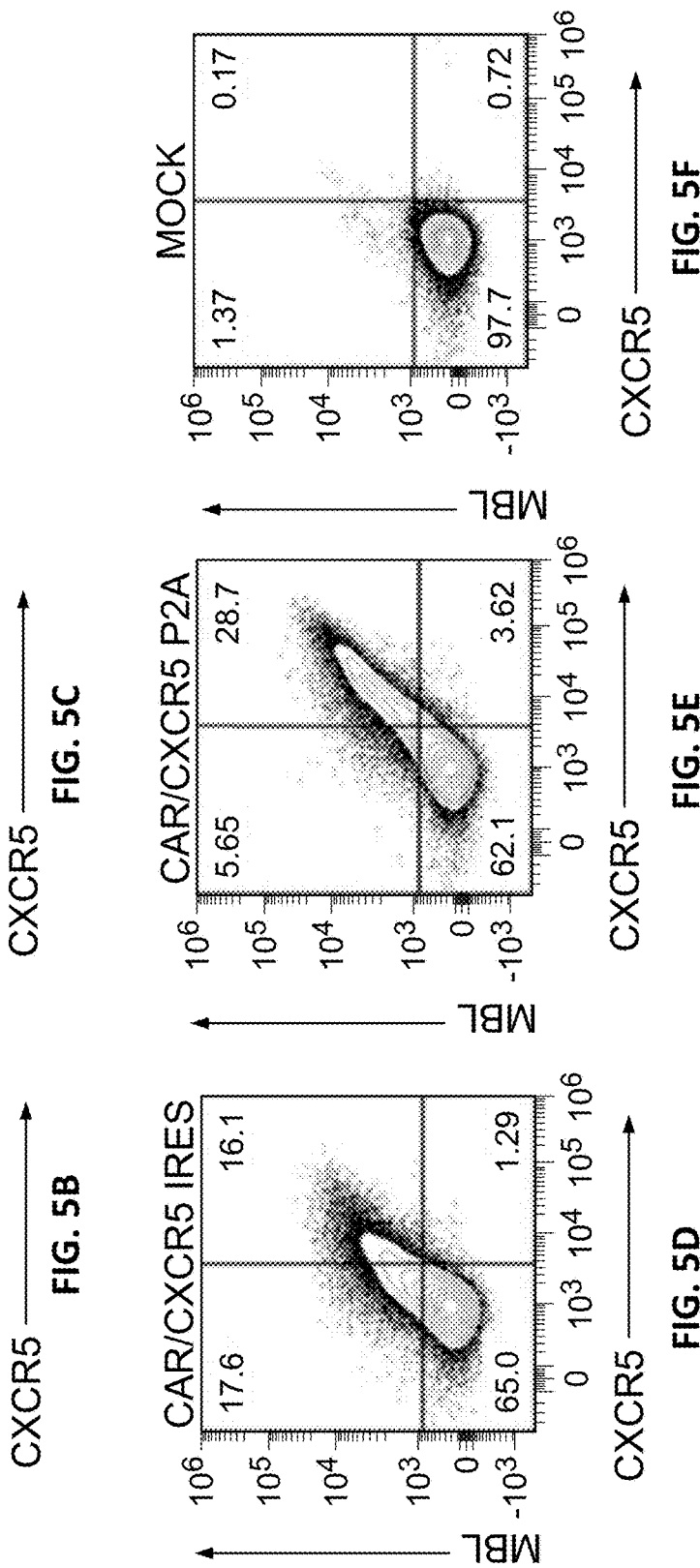

COMPOSITIONS AND METHODS FOR IMPROVING IMMUNOTHERAPY

CROSS REFERENCE TO RELATED APPLICATIONS

This application claims the benefit of priority under 35 U.S.C. § 119(e) to U.S. Application No. 62/514,438 filed Jun. 2, 2017.

FEDERALLY SPONSORED RESEARCH OR DEVELOPMENT

This invention was made with government support under AI096966, HL127479 and AI026617 awarded by the National Institutes of Health. The government has certain rights in the invention.

TECHNICAL FIELD

This disclosure generally relates to compositions and methods for improving immunotherapy.

BACKGROUND

An estimated 37 million people are currently infected with HIV-1 including more than 1 million in the United States. Last year, approximately 2 million people became infected with HIV and 1.2 million people died of AIDS. No effective vaccine has yet been developed for HIV. This is largely due to the high mutation rate of the virus. At this time, antiretroviral medications are necessary to suppress HIV-1 replication and prevent disease progression. However, antiretroviral medications must be taken lifelong and on a daily basis to be effective. These drugs are costly, frequently induce unpleasant or toxic side effects, must be taken with strict adherence to be effective, and are often rendered ineffective due to the development of drug resistance by the virus. These drugs are also not a cure. When taken off drugs, virus levels rebound and disease progression resumes, sometimes at an increased rate. The estimated cost of treating an HIV infected individual over their lifetime is estimated to approach $500,000. Thus, there is an urgent need to develop better treatment options and a cure for HIV.

SUMMARY

Compositions and methods for improving immunotherapy are described herein. For example, kits are provided that include vectors encoding a chimeric antigen receptor (CAR) construct and a CXCR5 polypeptide. The kits also can include any or all of the reagents needed to transduce cells. In addition, methods are provided that include transducing patient cells with a vector as described herein, followed by infusion back into the patient.

In one aspect, a CAR construct is provided that further includes a nucleic acid molecule encoding a CXCR5 polypeptide. In one embodiment, the CXCR5 polypeptide has the sequence shown in SEQ ID NO: 1 or 3. In one embodiment, the nucleic acid molecule encoding the CXCR5 polypeptide has the nucleic acid sequence shown in SEQ ID NO: 2 or 4. In some embodiments, the CAR construct is an HIV-based CAR construct. In some embodiments, the HIV-based CAR construct has the sequence shown in SEQ ID NO: 6, 8 or 10. In some embodiments, the HIV-based CAR construct is encoded by the nucleic acid sequence shown in SEQ ID NO: 7, 9 or 11.

In another aspect, a vector including a CAR construct and a nucleic acid molecule encoding a CXCR5 polypeptide is provided. In some embodiments, the vector is a lentiviral vector.

In still another aspect, a kit including a vector is provided. Such a vector typically includes a CAR construct and a nucleic acid molecule encoding a CXCR5 polypeptide. In some embodiments, a kit can further include reagents for transducing cells (e.g., patient T cells).

In yet another aspect, a method of inhibiting replication of HIV in cells is provided. Such a method typically includes providing cells from a subject having HIV; transducing the cells with a vector comprising a CAR construct and a nucleic acid molecule encoding a CXCR5 polypeptide; and culturing the cells. In some embodiments, the method can further include monitoring the cells for the presence of HIV In some embodiments, the method can further include monitoring the cells for the amount of HIV (particle number).

In one aspect, a method of (functionally) curing HIV in a subject is provided. Such a method typically includes infusing cells into the subject, wherein the cells are autologous to the subject and comprise a vector, and wherein the vector comprises a CAR construct and a nucleic acid molecule encoding a CXCR5 polypeptide. In some embodiments, the method can further include monitoring the subject for the presence of HIV. In some embodiments, the method can further include monitoring the subject for the amount of HIV (viral load).

In some embodiments, any of the methods described herein can further include obtaining the cells from the subject. In some embodiments, any of the methods described herein can further include transducing the cells with the vector.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A—Preliminary Results

FIG. 2A and FIG. 2B show the successful co-expression of an anti-HIV CAR and human CXCR5 in human PBMC. FIG. 2A are graphs showing the viability of the transduced cells (based on the mean fluorescent intensity of a live/dead cell stain that stains dead cells). FIG. 2B shows the transduction efficiency, with transduced cells detected using antibodies against MBL (for the CAR construct) and CXCR5. The CAR construct also expresses the ZSGreen reporter (not shown).

FIG. 3A are graphs showing the viability of the transduced cells (based on mean fluorescent intensity of a live/dead cell stain). FIG. 3B shows the transduction efficiency, with transduced cells detected using antibodies against MBL (for the CAR construct) and CXCR5. The CAR construct also induced expression of ZSGreen (not shown).

FIG. 4A-FIG. 4E shows that CXCR5 induced migration was detected in an ex vivo B cell follicle migration assay. Rhesus macaque PBMCs were transduced with CAR or CAR/CXCR5 vectors, labeled with CellTrace Violet (CTV), and layered onto freshly cut slabs of rhesus macaque lymph nodes. Panels A and B show tissues stained with anti-CD20 antibodies to delineate B cell follicles ("F") and anti-CD3 antibodies to delineate the T cell zone and extra-follicular areas ("EF"). Panel C shows that similar total levels of CFSE-labeled cells were detected in tissues treated with CAR or CAR/CXCR5 transduced cells. Panel D shows that, while CAR-transduced cells showed similar levels inside and outside of follicles, CAR/CXCR5-transduced cells primarily located within B cell follicles. Panel E shows that CAR/CXCR5-transduced cells exhibited much higher F:EF ratios compared to CAR-transduced cells.

Part B—Simian Immunodeficiency Virus (SIV)-Specific Chimeric Antigen Receptor-T Cells Engineered to Target B Cell Follicles and Suppress SIV Replication FIG. 5A is a schematic of the construct design, and expression in rhesus macaque T cells. Schematics showing constructs encoding the chimeric antigen receptor (CAR) (rhCD4-MBL CAR), rhCXCR5, and the bi-cistronic CAR/CXCR5 encoding both proteins, with CXCR5 expression mediated by IRES or P2A. In all cases, the targeting domains are linked to domains from rhesus CD28 including a short extracellular hinge, transmembrane TM, and cytoplasmic signaling, followed by the CD3 activation domain.

FIG. 5B-FIG. 5F are graphs of flow cytometry of cells transduced with gamma-retroviral vectors encoding (Panel B) CAR; (Panel C) CXCR5; (Panel D) CAR/CXCR5 (IRES); (Panel E) CAR/CXCR5 (P2A); or (Panel F) mock-transduced. Cells were pre-gated sequentially on lymphocytes, singlets, live cells, and CD3+ cells (T cells) and evaluated for CAR and CXCR5 expression using antibodies against mannose binding lectin (MBL) and CXCR5, respectively.

FIG. 6C shows the relationship between the percentage of cells expressing CXCR5 and the percentage of cells that migrated. In all panels, each data point symbol represents the mean value of duplicate samples obtained with cells from individual animals, with colors indicating transduction with CAR (blue) or CAR/CXCR5 (red).

FIG. 7A shows chimeric antigen receptor (CAR; left) or CAR/CXCR5-transduced (right) rhesus macaque CD8+ T cells stained with cell trace violet dye (CTV) (pseudo-colored yellow), pipetted on to fresh rhesus macaque lymph node sections and incubated for 6 h at 37° C. Sections were then fixed and stained with anti-CD20 antibodies (green) to delineate B cell follicles ("F") and anti-CD3 antibodies (blue) to delineate the T cell zone and extrafollicular areas ("EF"). Arrowheads indicate CTV+ cells. Confocal images were collected with a 20× objective. Scale bars equal 100 µm.

Part C—Nine Day Transduction and Expansion Protocol

Figure 9:
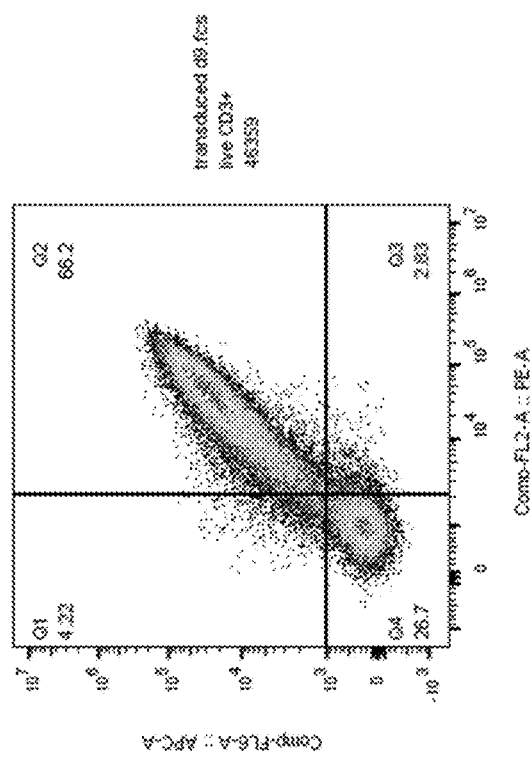

FIG. 9 shows flow cytometric analysis of Rhesus macaque PBMCs transduced and expanded in 9 days sorted on live, singlet, CD3 T cells co-labeled with MBL antibodies (binds CD4-MBL-CAR; x-axis) and CXCR5 antibodies (y-axis).

Figure 10:
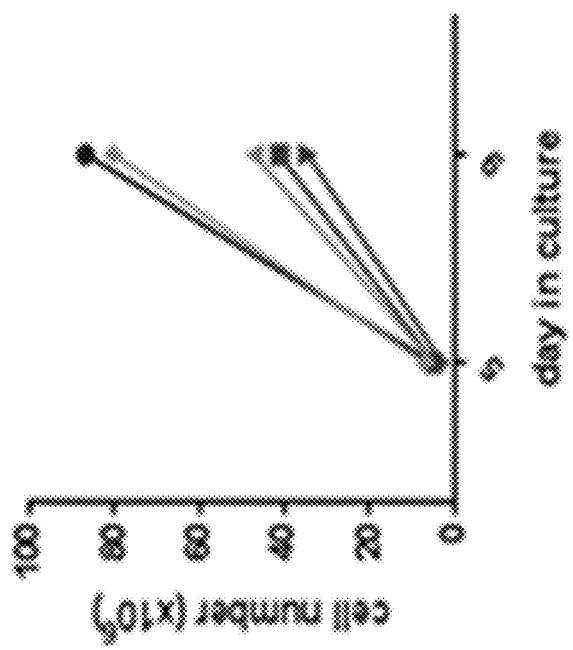

FIG. 10 shows that the 9-day protocol described herein yields sufficient cell numbers for cellular immunotherapy.

Figure 11:
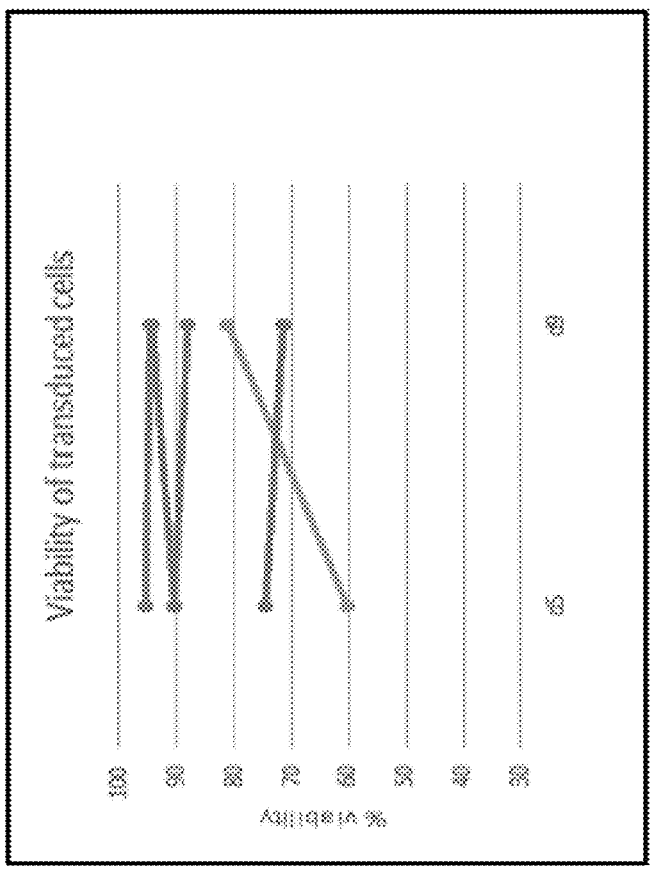

FIG. 11 shows that co-expression was maintained after the 9-day protocol described herein.

Figure 12:
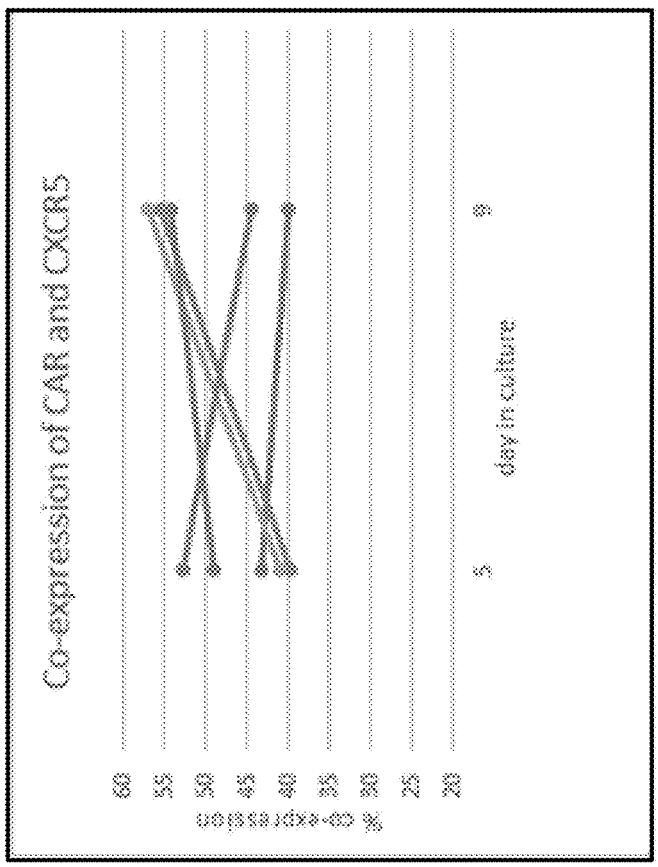

FIG. 12 shows that viability was maintained after the 9-day protocol described herein.

Figure 13:
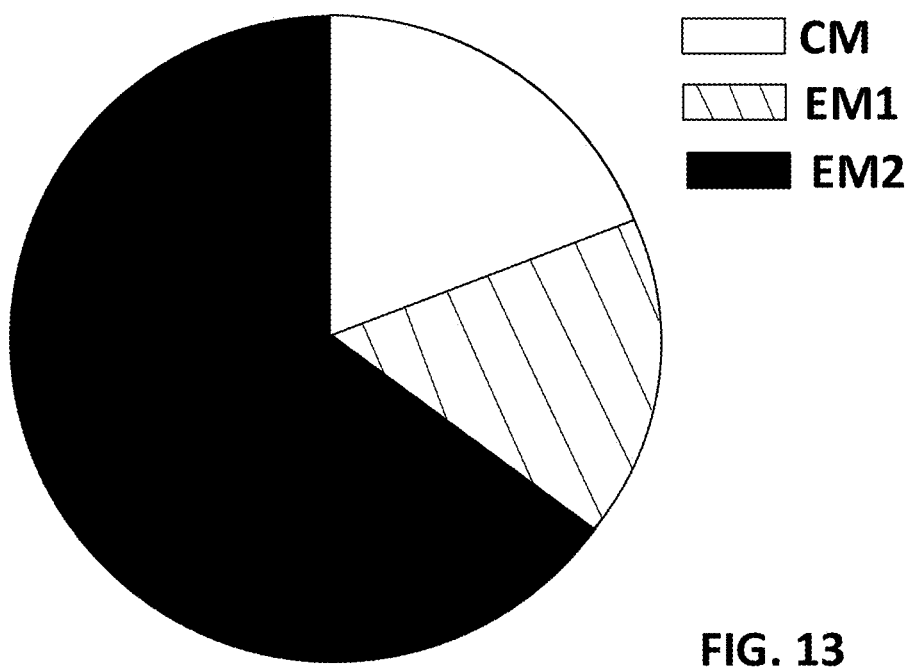

FIG. 13 showing representative result central memory T cells (TCM) maintained after 9 day transduction and expansion. Phenotype definitions: CM defined as CD95+, CD28+, CCR7+; EM1 defined as CD95+, CD28+, CCR7−; EM2 defined as CD95+, CD28−, CCR7−.

Figure 14:
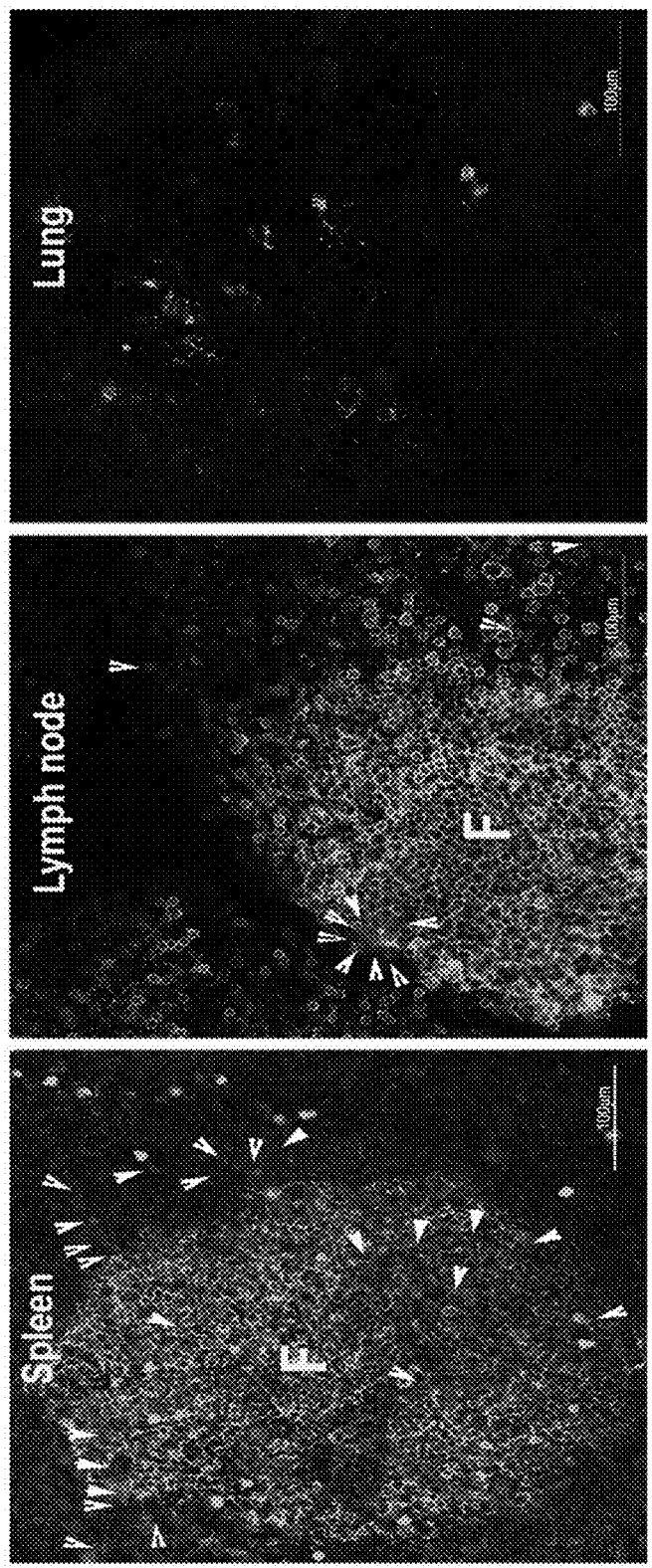

FIG. 14 shows CTV-labeled CD4-CD3-CAR/CXCR5-transduced PBMCs (pseudo-colored red and indicated with arrow heads) inside B cell follicles of spleen (left) and LN (middle) but not in lung (right). Sections were stained with either IgM antibodies or anti-CD20 antibodies to label B cells and identify follicles (F).

DETAILED DESCRIPTION

The methods described herein improve existing immunotherapy, particularly immunotherapy directed to B cells or B cell follicles. The methods described herein can be applied to any type of disease that includes B cell follicles, i.e., any type of disease in which the immunotherapy needs to reach B cell follicles, such as B cell lymphomas and other viral infections that include B cell follicles such as human immunodeficiency virus (HIV) or herpes viruses (e.g., HHV8, which causes Kaposi's sarcoma, or EBV, which can result in lymphomas).

The methods described herein are expected to result in a functional cure for HIV. As used herein, functional cure refers to suppressed viral replication in the absence of antiretroviral drugs. In some instances, functional cure refers to non-detectable levels of virus in the absence of antiretroviral drugs. Accordingly, the methods described herein can replace antiretroviral drug therapy to treat HIV The methods described herein are expected to be substantially cheaper and have fewer side effects than antiretroviral drug therapy, and are expected to replace the need for conventional drugs. As used herein, HIV refers to both HIV type 1 (HIV-1) and HIV type 2 (HIV-2).

During HIV infection, virus-producing cells accumulate inside B cell follicles within lymphoid tissues; the same is true in the simian immunodeficiency virus (SIV)-infected rhesus macaque model of HIV B cell follicles have been shown to be, at least to some extent, immune-privileged sites, in that CD8 T cells are largely excluded from B cell follicles, which thereby permit ongoing viral replication (Connick et al., 2007, J. Immunol., 178(11):6975-83)). The immune-privileged status of B cell follicles can explain the inability of HIV- and SIV-specific CD8 T cells to fully suppress virus replication.

Chimeric Antigen Receptor (CAR) T cell therapy is a type of immunotherapy that changes a subject's own T cells so they are better able to recognize and attack cancer cells or pathogens. It is demonstrated herein that engineering CAR-expressing CD8 T cells to also express CXCR5 (e.g., referred to herein as CAR/CXCR5 T cells) results in a substantial increase in the effectiveness of those immunotherapeutic T cells, to increase migration into B cell follicles. It has been shown that increasing levels of SIV-specific CD8 T cells in follicles is associated with a decrease in virus-producing cells in follicles, and also a decrease in plasma viral load. The same phenomena would be expected to occur in humans with HIV.

Thus, methods are provided that include collecting (e.g., obtaining, providing) cells from a subject having HIV, transducing those cells with both a CAR nucleic acid and a nucleic acid encoding a CXCR5 polypeptide, and returning those cells to the patient.

Cells collected from a subject can be any number of cells including, without limitation, a population of peripheral blood mononuclear cells (PMBCs; e.g., CD8 T cells, CD4 T cells and a few NK cells) or T cells (e.g., CD8 T cells). In addition or as an alternative to T cells, the methods described herein can be applied to NK cells (e.g., autologous or allogeneic NK cells) and/or hematopoietic stem cells (HSCs). This method also could be applied to engineered T cells that are not specific for a particular subject (e.g., universal T cells).

Cells can be collected from a subject using known methods. Typically, cells are collected in a biological sample. Biological samples can include, without limitation, blood, serum, cerebrospinal fluid, or tissues (e.g., tissue biopsy, e.g., muscle biopsy, skin biopsy). In some instances, apheresis is used to obtain the desired cells from the blood of a subject, which then can be returned back to the subject.

Following collection, cells can be transduced with one or more nucleic acid vectors or constructs (e.g., a CAR/CXCR5 construct, or a CAR construct and a construct encoding CXCR5). Methods of transducing cells are known in the art. For example, and without limitation, cells can be transduced with one or more nucleic acid molecules using, for example, mechanical means (e.g., electroporation), viral mechanisms (e.g., retroviruses carrying the CAR/CXCR5 construct), or gene editing (e.g., CRISPR or TALEN) (see, for example, Eyquem et al., 2017, Nature, 543:113-7).

CAR constructs are known in the art, and typically include an antigen-binding targeting portion, sometimes referred to as a ligand-binding targeting portion, and a signaling domain that results in T cell activation following binding by the antigen. The signaling domain can be a transmembrane domain, a cytoplasmic domain, or an intracellular domain.

CAR constructs and methods of making CAR constructs are known in the art. See, for example, Brentjens et al., 2010, Mol. Ther., 18:4:666-8; Till et al., 2008, Blood, 12:2261-71; Park et al., 2011, Trends Biotechnol., 29:550-7; Grupp et al., 2013, N. Engl. J. Med., 368:1509-18; Han et al., 2013, J. Hematol. Oncol., 6:47; Tumaini et al., 2013, Cytotherapy, 15:1406-17; Haso et al., 2013, Blood, 121:1165-74; WO 2012/079000; WO 2013/059593; US 2012/0213783; and U.S. Pat. No. 9,629,877, all of which are incorporated herein by reference in their entirety.

Specifically with respect to HIV, there are a number of CAR constructs that are known in the art. For example, and without limitation, see Liu et al., 2015, J. Virology, 89(13): 6685-94; Hale et al., 2017, Mol. Ther., 25(3):570-9; Zhen et al., 2015, Mol. Ther., 23(8):1358-67; U.S. Pat. Nos. 7,115, 262; 7,151,087; and 8,420,099; US 2013/0189264; and US 2017/0267739, all of which are incorporated herein by reference in their entirety. A number of representative HIV CAR constructs are shown in SEQ ID NOs: 6, 8 and 10, which are encoded by the HIV CAR nucleic acid constructs shown in SEQ ID NOs: 7, 9 and 11, respectively. Representative HIV CAR constructs are described in more detail in WO 2015/077789.

A CAR construct (e.g., an existing CAR construct) can be genetically engineered to also include a nucleic acid molecule encoding a CXCR5 polypeptide, or a new vector can be generated that includes the necessary components of a CAR construct as well as a nucleic acid molecule encoding a CXCR5 polypeptide. Representative human CXCR5 polypeptides are shown in SEQ ID NO:1 (i.e., GenBank Accession No. NP_001707.1) and SEQ ID NO:3 (i.e., GenBank Accession No. NP_116743.1), which are encoded by the nucleic acid sequences shown in SEQ ID NO:2 (i.e., GenBank Accession No. NM_001716.4) and SEQ ID NO:4 (i.e., GenBank Accession No. NM_032966.2).

In some instances, it may be desirable to codon optimize the CXCR5 nucleic acid sequence and/or the CAR construct. Codon optimization is known in the art and can be performed using, for example, computer software. A representative computer software for codon optimizing a sequence can be obtained from IDT (see, for example, idtdna.com/CodonOpt on the World Wide Web), but others are available. An example of a codon optimized human CXCR5 sequence is shown in SEQ ID NO: 5.

In some embodiments, a nucleic acid encoding a further polypeptide can be delivered to the T cells (e.g., CD4 T cells) such that the T cells are made resistant to infection by HIV See, for example, Hale et al. (2017, Mol. Ther., 25:570); and Younan et al. (2013, Blood, 122:179-87). A representative further polypeptide that can impart resistance to HIV infection by T cells is the mC46 polypeptide. A further polypeptide, whether it be to impart resistance to infection by HIV or for another purpose, can be included in the CAR/CXCR5 construct (e.g., under one of the existing promoters or under a different promoter) or, if CAR and CXCR5 are delivering on separate constructs, the further polypeptide can be included in one or the other or both of those constructs. Alternately, a further polypeptide can be included and delivered to the cells in its own construct.

Such a construct (e.g., CAR/CXCR5) or constructs (e.g., a CAR and a CXCR5) can be contained within a host cell or a virion for propagation outside of T cells and/or for maintenance in the T cells.

Methods of culturing and expanding the transduced cells are known in the art. In some instances, it may be desirable to include, without limitation, IL-15 or ALT-803, an IL-15 superagonist (NantKwest) in the culture. In some instances, it may be desirable to switch the cytokines that are present in the media during the culturing of the cells, which may lead to increased persistence of cells and fewer regulatory T cells (Treg cells). For example, various combinations of IL-15, IL-7, and/or IL-21, with or without IL-2, can be used in the culture media.

Following transduction of the patients' cells and appropriate culturing and expansion of the transduced cells, those cells are returned back to the same patient. Returning cells to a patient is oftentimes performed via infusion. Infusion is known in the art, and typically includes suspending the cells in a pharmaceutically acceptable carrier and introduced the composition back into the subject intravenously. Pharmaceutically acceptable carriers are known in the art and include, without limitation, saline or other physiological buffers, nutrients, preservatives, and the like.

In some instances, it may be desirable to lymphodeplete the subject prior to cellular immunotherapy to create space for the homeostatic proliferation of the infused cells. For example, lymphodepletion can be achieved using a chemotherapeutic such as cyclophosphamide (e.g., Cytoxan) or, alternatively, an anti-CD20 antibody (e.g., Rituximab), which can temporarily deplete B cells and B cell follicles (i.e., the virus-producing cells).

As demonstrated herein, those T cells (e.g., CAR/CXCR5 T cells) migrate to B cell follicles and are able to significantly suppress the replication of HIV. As a part of the methods described herein, a subject can be monitored for the presence and/or amount (e.g., viral load) of HIV. In addition, because of the precise targeting provided by CXCR5, subjects receiving a CAR/CXCR5 construct as described herein would not require intravenous immunoglobulin (IVIG) treatments, as is needed for B cell depleting CARS like CD19-specific CARs, as they would not remain immunocompromised. For example, subjects (e.g., virally suppressed subjects on cART or infected subjects who have not received cART) can be infused with CAR/CXCR5 T cells (e.g., autologous CAR/CXCR5 T cells) or CAR/CXCR5 NK cells (e.g., autologous or allogeneic CAR/CXCR5 NK cells) as described herein. Upon receiving the CAR/CXCR5 T cells or CAR/CXCR5 NK cells, the subject typically will no longer receive antiviral therapy. The autologous CXCR5/CAR T cells, or autologous or allogeneic CAR/CXCR5 NK cells, home to lymphoid B cell follicles, where HIV-producing cells are most concentrated, and suppress viral replication. In many subjects, immunotherapy, which is significantly improved by the presence of the CXCR5 polypeptide described herein, can lead to a functional cure of HIV In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A—Preliminary Results

Example 1-CAR/CXCR5 Vectors and Transduced Cells

An HIV-1-specific CAR has been developed (Liu et al., 2015, J. Virology, 89(13):6685-94). In the field, CAR constructs have been generated in both a lentiviral vector background as well as a mouse gamma retroviral vector background. These vectors have been constructed with an internal ribosome entry site (IRES) to drive expression of CXCR5 with the CAR or with a protease cleavage site from which co-expressed proteins get cleaved by cellular proteases after expression. See, for example, Vagner et al., 2001, EMBO Reports, 2:893-8; Chinnasamy et al., 2006, Virology J., 3:14.

Virus binding is primarily mediated by interaction of gp120, the external subunit of the HIV envelope glycoprotein (Env) with CD4 protein and various coreceptor molecules (one of several alternative chemokine receptors). These interactions then activate the gp41 transmembrane subunit of the envelope glycoprotein, to cause fusion between the virus and cell membranes.

Figure 1A:
FIG. 1A and FIG. 1B are schematics showing a representative genetic CAR construct composed of a targeting region consisting of an extracellular region of CD4 (domains 1+2) attached to the carbohydrate-recognition domain of mannose-binding lectin (MBL), followed by a transmembrane (TM) and intracellular signaling domains from CD28 and CD3 zeta chain. The CAR construct is followed by an internal ribosome entry site for translation of a second gene, the ZSGreen reporter (FIG. 1A) or the IRES-driven CXCR5 (FIG. 1).
Figure 1B:

Human CXCR5 (SEQ ID NO:2) was sub-cloned into the plasmid vectors containing the HIV-specific CAR, and rhesus CXCR5 (encoding the polypeptide shown in GenBank Accession No. XP_001100017) was sub-cloned into the vectors containing the SIV-specific CAR to generate HIV- and SIV-based CXCR5/CAR vectors, respectively. FIG. 1 is a schematic of two of these vectors; FIG. 1A shows a SIV-based CAR vector (Rh CD4 MBL2 CAR), while FIG. 1B shows a SIV-based CXCR5/CAR vector (Rh CD4 MBL2 CAR+CXCR5). The plasmid vectors were verified by sequencing, used to generate pseudotyped retroviral vectors, and the virions were produced and titrated.

Figure 3A:
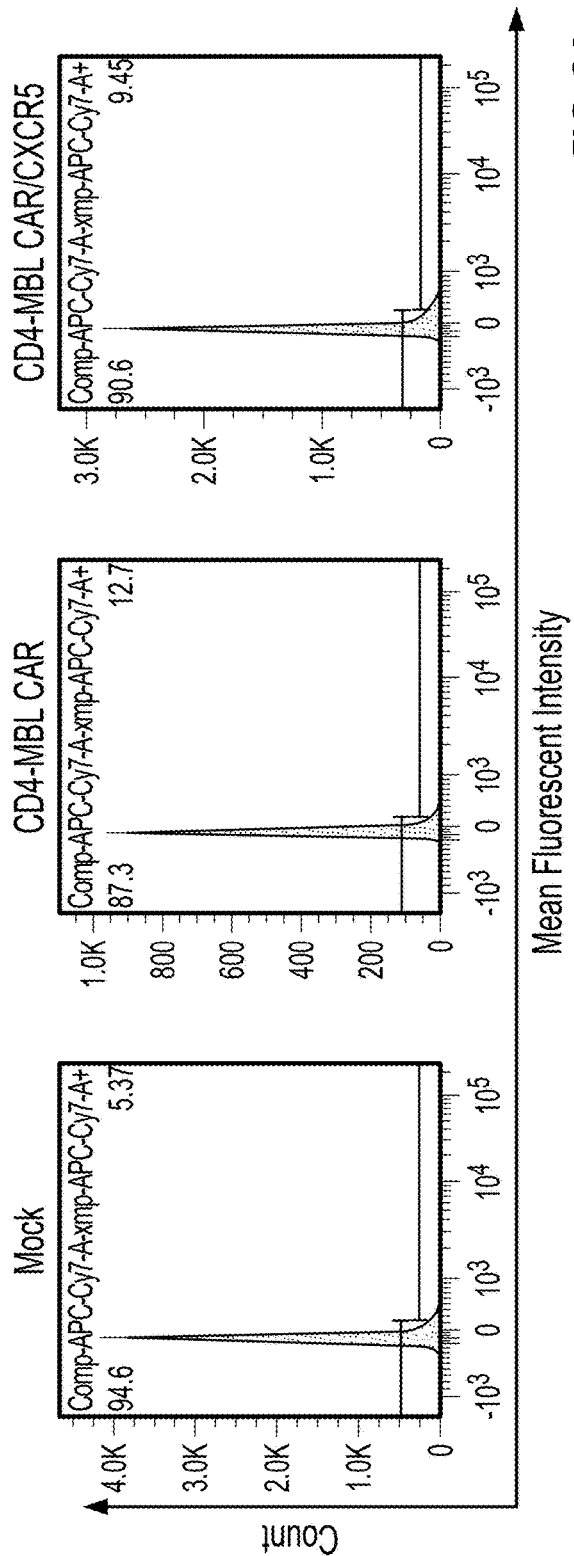
FIG. 3A and FIG. 3B show the successful co-expression of an anti-SIV CAR and rhesus CXCR5 in rhesus PBMC.
Figure 3B:
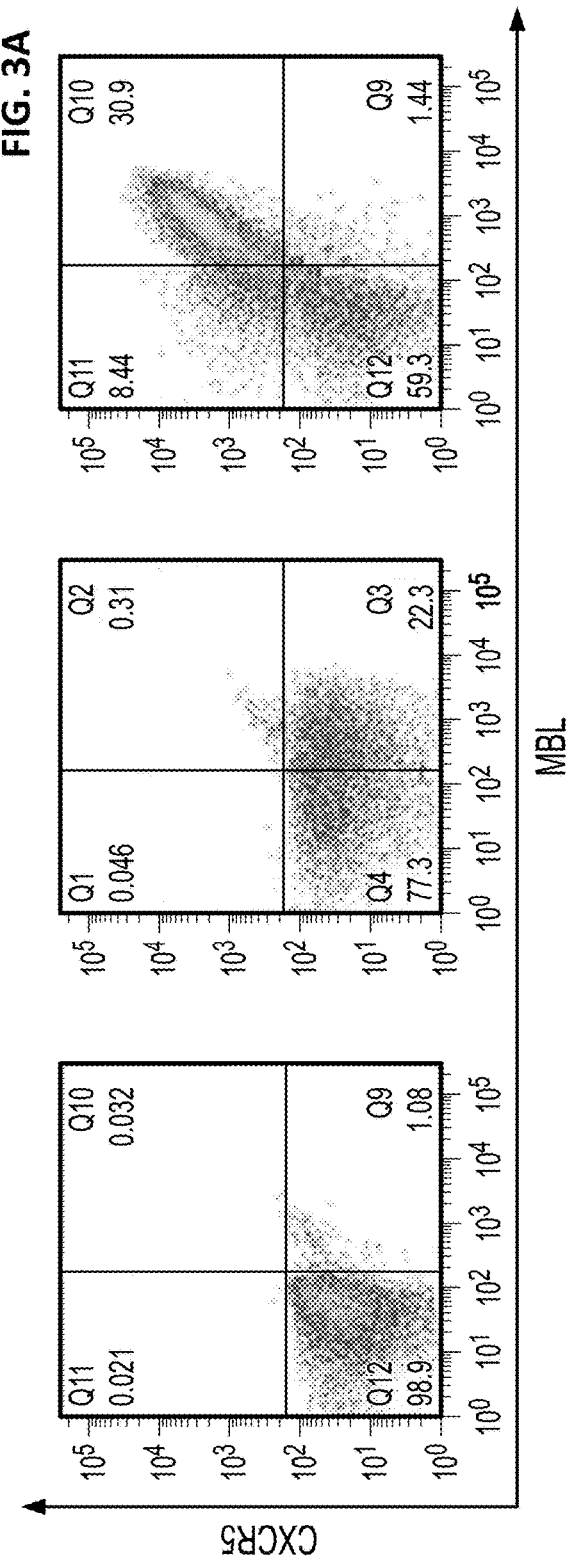

Primary CD8 T cells from humans and rhesus macaques then were transduced with each vector (or a CAR-only vector). Transduction efficiency was determined by staining transduced (and mock-transduced) cells with antibodies directed against CXCR5 and CAR. The viability of transduced cells was determined using a live-dead cell stain. FIG. 2 shows the co-expression of human CAR and CXCR5 in human PBMC, and FIG. 3 shows the co-expression of corresponding rhesus proteins in rhesus PBMC.

Example 2—Efficacy of CAR/CXCR5 Vector Transduced Cells

A comprehensive multicolor flow cytometric analysis of CXCR5-transduced cells is performed to determine the percentage and viability of transduced cells, as well as CD8 naïve, regulatory, memory, and memory stem cell subsets. Such flow cytometry strategies are well-established (Sallusto et al., 2004, Annu. Rev. Immunol., 22:745-63).

Efficacy of the CAR/CXCR5 T cells can be demonstrated by showing that the CAR/CXCR5-transduced T cells 1) migrate towards the ligand for CXCR5, CXCL13; 2) migrate to B cell follicles in tissues processed in the lab; and/or 3) migrate to B cell follicles in SIV-infected rhesus macaques.

The ability of transduced cells to migrate towards CXCL13 is assessed using a transwell chemotaxis assay as previously described (Meditz et al., 2008, AIDS Res. Hum. Retrovir., 24(7):977-85).

Migration of CAR/CXCR5 transduced cells into B cell follicles was also demonstrated in an ex vivo migration assay. Here, rhesus macaque PBMCs were transduced with CAR or CAR/CXCR5 vectors, labeled with CTV, and dripped onto slabs of fresh rhesus macaque lymph nodes. Tissues were subsequently stained with anti-CD20 antibodies to delineate B cell follicles ("F") and anti-CD3 antibodies to delineate the T cell zone and extra-follicular areas ("EF") (FIGS. 4A and 4B). Similar total levels of CTV-labeled cells were detected in tissues treated with CAR and CAR/CXCR5 transduced cells (FIG. 4C). CAR-transduced cells showed similar levels in follicles and outside of follicles, whereas CAR/CXCR5-transduced cells primarily located within B cell follicles (FIG. 4D). CAR/CXCR5-transduced cells showed much higher F:EF ratios compared to CAR-transduced cells. Thus, these experiments demonstrated that CXCR5 induced migration in an ex vivo B cell follicle migration assay.

Example 3—Treatment of SIV-Infected Rhesus Macaque

Chronically SIVmac239- or SIVmac251 infected rhesus macaque are treated with CXCR5/CAR transduced cells. CXCR5/CAR T cells are labeled with a live cell stain, such as CFSE or CTV, prior to infusion so that the cells can be tracked. CXCR5/CAR T cells, CD4 and CD8 T cell counts, and viral loads in blood are evaluated before treatment and, following treatment, are monitored over time. In addition to blood PBMC, CXCR5/CAR cells are tracked and quantified in lymphoid tissues (lymph node, spleen, GALT), and bronchoalveolar lavage (BAL) at multiple time points using flow cytometry (using CFSE+CD8+CXCR5+CD4+MBL+). On day 60 following the infusion, the animal is sacrificed and a necropsy performed in which multiple tissues are collected and examined. The tissues that are collected include lymph nodes (inguinal, axillary, iliac, mesenteric), spleen, gut associated lymphoid tissues, liver, brain (obex) and lung.

In tissues, transduced cells are visualized in situ using CFSE and immunostaining with antibodies (e.g., the antibodies described above for use in flow cytometry) in combination with anti-CD20 to define B cell follicles morphologically as previously described (Connick et al., 2007, J. Immunol., 178)11):6975-83). In addition, anti-FITC antibodies may be used to amplify weak signal from CFSE-labeled cells that have gone through multiple cell divisions. As a secondary means to track transduced cells in tissues, in situ hybridization with a probe specific for the retroviral vector, combined with anti-CD20 staining, can be performed as described (Connick et al., 2007, J. Immunol., 178)11): 6975-83). Similarly, SIV producing cells are quantified in tissues using in situ hybridization as described (Connick et al., 2007, J. Immunol., 178)11):6975-83).

Part B—Simian Immunodeficiency Virus (SIV)-Specific Chimeric Antigen Receptor-T Cells Engineered to Target B Cell Follicles and Suppress SIV Replication Example 4—Plasmid Constructs and Retroviral Vectors Encoding CARs All CAR targeting motifs were synthesized by GenScript, codon-optimized for expression in rhesus macaque cells, and sub-cloned into the plasmid pMSGV1 gamma-retrovirus vector backbone (Hughes et al., 2005, Hum. Gene Ther., 16:457-72). The active antiviral CAR employed in this study was a rhesus variant of the human bispecific CAR designated CD4-MBL (Ghanem et al., 2017, Cytother., doi: 10.1016/j.jcyt.2017.11.001). As a non-reactive negative control, the previously described 139 CAR was used, which does not react with cells in this system. The targeting domains were linked to extracellular hinge, transmembrane and cytoplasmic co-stimulatory domain of rhesus CD8 followed by the activation domain of rhesus CD3 zeta, as previously described (Liu et al., 2015, J. Virol., 89:6685-94; Ghanem et al., 2017, Cytother., doi:10.1016/j.jcyt.2017.11.001).

T cells were transduced to express either the rhCD4-MBL CAR, rhCXCR5, or the rhCD4-MBL CAR plus rhCXCR5. For co-expression, bi-cistronic plasmid constructs (produced by GenScript) were designed in which the rhCD4-MBL gene was linked to the downstream rhCXCR5 gene. CXCR5 expression was driven by either the ECMV internal ribosome entry site (IRES) or the self-cleaving P2A peptide from porcine teschovirus-1 with a GSG linker added at the N-terminus of the P2A peptide sequence (Kim et al., 2011, PLoS One, 6:e18556). The corresponding gamma-retroviruses were generated for expression of these genes in rhesus macaque T cells. In most experiments, these plasmids were co-transfected with the plasmid pBS-CMV-gagpol (Delang et al., 2016, Sci. Rep., 6:31819) (a gift from Dr. Patrick Salmon, Addgene plasmid #35614), a plasmid encoding RD114 envelope glycoprotein (Porter et al., 1996, Hum. Gene Ther., 7:913-9), and the plasmid pMD.G encoding VSV-G envelope (Gori et al., 2007, J. Pharmacol. Exp. Ther., 322:989-97) (a gift from Dr. Scott McIvor) at ratios of 3:1:1:0.4, respectively. Retroviral vector supernatants were collected 48 h after transfection, and were titrated by transducing HEK293T cells. Retrovirus was snap frozen and stored at $-80°$ C. In the SIV suppression studies, gamma-retrovirus vector production was carried out as previously described (Liu et al., 2015, J. Virol., 89:6685-94).

Example 5—Transduction of Rhesus T Cells

Primary rhesus macaque PBMC, or CD8+ T cells enriched by negative selection (Miltenyi), were activated for 2 to 3 days in six-well plates with plate-bound anti-CD3 (FN18) and soluble anti-CD28.2 (both from NUP Reagent Resource) in either RPMI supplemented with 10% heat inactivated FBS, 100 U/ml penicillin, 100 µg/ml streptomycin, and 300 IU/ml IL-2, for early experiments, or in X-Vivo 15 completed with 10% heat inactivated FBS, 100 U/ml penicillin, 100 µg/ml streptomycin, 2 mM glutamine, and 50 IU/ml IL-2 for later experiments. RetroNectin (TaKaRa)-mediated transduction was carried out on the activated T cells. Retroviral vector supernatants, diluted in serum-free media, were added (eventual MOI of 0.5) to RetroNectin-coated six-well plates and centrifuged for 2 h at 2,000×g to facilitate binding of the retrovirus. After removal of the unbound retrovirus, activated PBMC or CD8+ T cells (1.5×

10E6 cells/well) were added to the wells and centrifuged at 1,000×g for 10 min. Mock-transduced cells were subjected to exactly the same procedures without the addition of retrovirus to the RetroNectin-coated wells. Cells were cultivated in the media listed above for 5-6 days prior to analysis by flow cytometry.

Example 6—Flow Cytometry

Cells were analyzed using an LSR Fortessa flow cytometer (BD Bioscience). The following antibodies were used: CD4 (M-T477, reactive with endogenous rhCD4 and the rhCD4-MBL CAR), CD3 (SP34-2), CD8 (RPA-T8) (all from BD Bioscience), CXCR5 (MU5UBEE) (eBioscience), MBL2 (3E7) (Invitrogen). Viability was assessed with the Live/Dead Fixable Near IR Dead Cell Stain Kit (Invitrogen). A minimum of 70,000 events were acquired for each sample. Data analysis utilized FlowJo v10 (FlowJo, LLC).

Example 7—In Vitro Transwell Migration Assay

Rhesus macaque PBMCs were transduced with the CAR or CAR/CXCR5 vectors, or mock-transduced. Samples were run in duplicate. For each sample, one million cells in 100 µl X-Vivo-15 media containing 0.1% BSA were placed in the upper chamber of a 24-well plate, with a 5.0 µm transwell membrane (Costar). To the lower chamber containing 600 µl X-Vivo 15 and 0.1% BSA, either CXCL12 at 1 µg/ml or CXCL13 at 2.5 µg/ml (both from ProSpec) were added. No chemokine was added to control wells. After incubation for 4 h at 37° C., cells were collected from the lower chamber, fixed with 1% paraformaldehyde, and counted on a Cytoflex flow cytometer (Beckman). All samples were normalized with the addition of AccuCheck Counting Beads (Invitrogen). Specific cell migration was determined by first subtracting the number of cells that migrated to media alone from the number of cells that migrated to the chemokine and then dividing by the number of cells added to the upper chamber.

Example 8—Ex Vivo B Cell Follicle Migration Assay

Chimeric antigen receptor- and CAR/CXCR5-transduced rhesus CD8+ T cells were used in conjunction with fresh lymph node tissue sections from allogeneic rhesus macaques. A gelatin sponge (7 mm Gel foam by Pfizer) was cut to fit and placed into a six-well plate containing 3-4 ml of RPMI with 20% heat inactivated FBS. The sponge was hydrated for 1 h at 37° C. Fresh rhesus macaque lymph nodes, collected at the Wisconsin National Primate Research Center, were shipped in chilled RPMI containing 100 µg/ml heparin overnight on ice blocks. Lymph nodes were cut into 0.5 cm×0.5 cm pieces and embedded in 40° C. PBS-buffered 4% low-melt agarose and cut into 300-µm thick slices using a Compresstome, as previously described (Abdelaal et al., 2015, Biol. Proced. Online, 17:2). Tissue sections and associated agarose were laid flat on the hydrated sponge without being submerged. Transduced CD8+ T cells were stained with a 5-µM solution of Cell Trace Violet Dye (CTV) (Molecular Probes). The dye was added at a 1:1 ratio to 1×10E7 cells/ml suspended in PBS/10% FBS, and cells were incubated for 15 min at 37° C., followed by two washes with complete RPMI supplemented with 10% heat inactivated FBS 100 U/ml penicillin, and 100 µg/ml streptomycin. For each fresh tissue section, one million CTV-stained transduced CD8+ T cells were re-suspended in 20-30 µl complete RPMI and were slowly pipetted onto the surface of the tissue. Tissue sections were incubated at 37° C. for 6 h followed fixation with 4% PBS-buffered paraformaldehyde for 2 hours at room temp. After fixation, sections were washed with chilled PBS containing 100 µg/ml heparin (PBS-H). Antigen retrieval was carried out by boiling tissues 3× in 0.01 M urea for 30 s. Tissues were permeabilized and blocked with PBS-H containing 0.3% Triton x-100 and 2% normal goat serum for 1 h, then incubated overnight with mouse-anti-human CD20 (0.19 µg/ml, clone L26, Novocastra) to label B cells and rat-anti-human CD3 (2 µg/ml, CD3-12, Bio-Rad) to label T cells. After washing with PBS-H, secondary antibody staining was carried out by incubating tissues overnight with goat-anti-mouse-IgG/Alexa 488 (0.75 µg/ml Jackson ImmunoResearch Laboratories) and goat-anti-rat-IgG/Cy5 (0.3 µg/ml, Jackson ImmunoResearch Laboratories). All incubations were done at 4° C. on a rocking platform. Sections were imaged using a Leica confocal microscope. 512×512 pixel z-series were collected using a step size of 2 µm and with collection initiated at least 50 µm deep into each section. B cell follicles were identified morphologically as clusters of brightly stained closely aggregated CD20+ cells. Areas that showed loosely aggregated B cells that were ambiguous as to whether the area was a follicle were not included. Cell counts were done with individual z-scans. The total number of CTV-stained cells was counted inside follicles and the adjacent area outside of the follicles. For each sample, 2-3 tissue sections and a minimum of three follicles (range 3-8) were evaluated.

Example 9-SIV Suppression Assay

To generate SIV-infected target cells, rhesus macaque PBMCs were re-suspended at 5×10E5/ml in complete medium, transferred to a T25 flask, and incubated at 37° C. in 5% CO2 for 2-3 days. The PBMCs were washed, adjusted to 3×10E6/ml in total of 4 ml volume in complete media containing 30 IU/ml IL-2, and incubated with 200-600 TCID50/ml of virus for 24 h at 37° C. in 5% CO2. Infected cells were washed three times using 20 ml of medium per wash and then re-suspended in complete medium at a density of 1.5×10E6 cells per ml in 96-well round bottom plates. To generate effector cells, T cells (derived from activated PBMCs) were transduced with the indicated gamma-retroviral vectors. In triplicate, 100 µl of SIV-infected targets were mixed with 100 µl of serially diluted effectors. Co-cultures were incubated at 37° C. in 5% CO2 for a total of 16 days. On the indicated days, supernatants were collected, and p27 content was determined by ELISA (ABL, Inc.).

Example 10—Statistical Analysis

All statistical analyses assumed two-sided tests with P<0.05 considered significant. Paired t-tests with pooled variance were used to evaluate co-expression levels of the CAR and CXCR5 via IRES versus P2A constructs. An unpaired t-test with pooled variance was used to evaluate groups in the CXCL12 in vitro migration assays while an unpaired Welch's t-test of unequal variance was used to evaluate groups in the CXCL13 in vitro migration assays. Paired t-tests with pooled variance were used in all statistical analyses in the ex vivo migration assay. The F:EF ratios were log transformed before analysis. Statistical analyses were conducted using GraphPad Prism (Version 6.01; GraphPad Software, Inc., La Jolla, CA, USA).

Example 11—Results

The goal of this work was to engineer rhesus macaque T cells to co-express a potent anti-SIV CAR along with CXCR5, in order to promote CAR-T cell trafficking to B cell follicles. To this end, constructs for expression of the CARs were designed, with or without co-expression of CXCR5. CAR-transduced T cells were analyzed using both an in vitro trans-well assay of chemokine-directed cell migration and a novel ex vivo B cell follicle migration assay. In addition, the ability of T cells expressing CAR and CXCR5 to suppress viral replication was tested in vitro.

Example 12-CAR and CXCR5 Expression in Transduced Primary Rhesus Macaque T Cells Gamma-retroviral vectors encoding the rhCD4-MBL CAR and rhCXCR5 constructs were developed, and vectors encoding bicistronic constructs to express both proteins were developed. Two variations of bicistronic vectors were developed, one with CXCR5 co-expression driven by an internal ribosome entry site (IRES) and the other via a P2A self-cleavage site (Kim et al., 2011, PLoS One, 6:e18556). For simplicity, the constructs encoding the rhCD4-MBL CAR alone or the bicistronic rhCD4-MBL CAR plus rhCXCR5 are, respectively, referred to as CAR or CAR/ CXCR5; for the latter, the use of either the IRES or P2A modalities is indicated. The constructs are shown schematically in FIG. 5A.

Figure 5H:
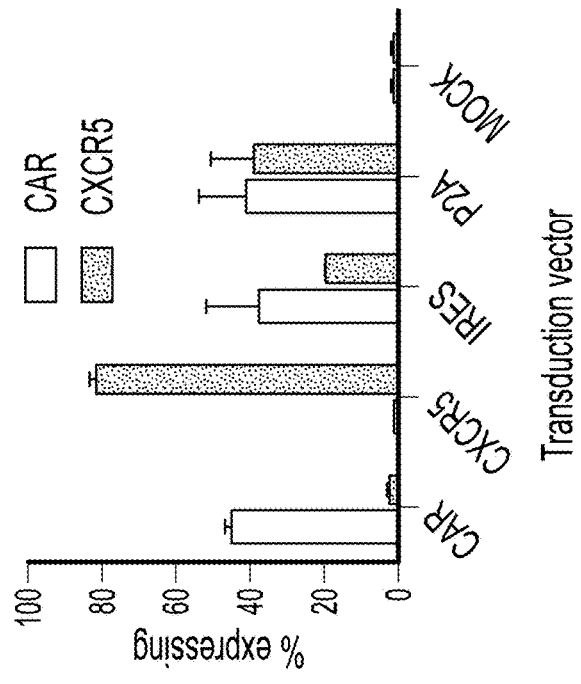
FIG. 5H is a graph of the median percentage of T cells that expressed the CAR and CXCR5 in activated PBMCs transduced with CAR (n=3), CXCR5 (n=3), CAR/CXCR5 (IRES) (n=5), CAR/CXCR5 (P2A) (n=5) and mock-transduced (n=5).
Figure 5I:
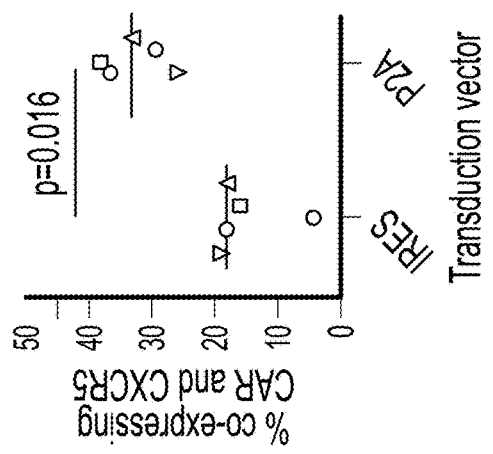
FIG. 5I shows the percentage of T cells that co-expressed the CAR and CXCR5 in activated PBMCs transduced with either CAR/CXCR5 (IRES) or CAR/CXCR5 (P2A).
Figure 5G:
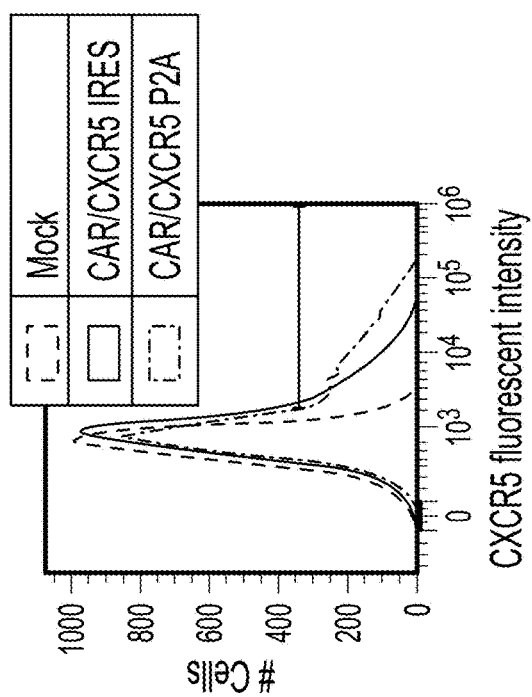
FIG. 5G is a histogram depicting fluorescent intensities of CXCR5 expression from samples shown in Panels D-F.

In FIGS. 5B-5F, T cells derived from activated rhesus PBMCs were transduced with gamma-retroviral vectors encoding the CAR or CXCR5 genes alone, or the bi-cistronic CAR/CXCR5 constructs (IRES or P2A). Cell viabilities post-transduction were 87-90% (data not shown). Antibodies directed against MBL or CXCR5 were used to detect surface expression of the CAR and CXCR5, respectively. Transduction with the CAR (FIG. 5B) or CXCR5 (FIG. 5C) vectors gave the expected surface expression of the corresponding individual proteins. For vectors encoding the bi-cistronic CAR/CXCR5, the P2A-based construct yielded a clear population of cells expressing both CAR and CXCR5, with only a small fraction of cells expressing only one of the proteins; by contrast. The IRES-based construct appeared less effective at co-expressing CXCR5 relative to CAR, since the fraction of cells expressing only the CAR was comparable to that expressing both proteins, with a minimal fraction expressing only CXCR5 only (FIGS. 5D, 5E). These results are consistent with the efficient P2A system producing equivalent amounts of the two post-cleavage components of a bi-cistronic construct, as contrasted with the relatively inefficient expression of the downstream component in the IRES system (Mizuguchi et al., 2000, Mol. Ther., 1:37-82; Ibrahimi et al., 2009, Hum. Gene Ther., 20:845-60). Moreover, as indicated in FIG. 5G, the P2A-based construct produced cells with nearly twofold higher surface expression levels of CXCR5 than obtained with the IRES-based construct (median 1.8-fold higher; range 1.4- to 2.2-fold).

The percentages of T cells that expressed the CAR and CXCR5 with each construct are shown in FIG. 1H. Transduction with the vectors encoding CAR-only or CXCR5-only yielded a median of 44.4% (range 40-47.6%) and 81.1% (range 51.8-84.2%) of cells expressing each protein, respectively. Cells transduced with the IRES-based bi-cis-tronic CAR/CXCR5 vector showed higher number of cells expressing the CAR compared to CXCR5, with a median cell expression of 37.2% (range 5.6-50.2%) for the CAR and 19.4% (range 4.7-19.7%) for CXCR5. In contrast, cells transduced with the P2A-based CAR/CXCR5 vector showed similar expression of the two proteins, with a median of 40.2% (range 37.3-52.2%) for the CAR and 38.9% (range 27.5-50.2%) for CXCR5. Similar transduction efficiencies were found with enriched rhesus CD8 T cells transduced with these vectors (data not shown). The percentage of cells that co-expressed CAR and CXCR5 is shown in FIG. 5I. Cells transduced with the IRES-based construct showed a median co-expression efficiency of 18.1% (range 4.3-18.9%), whereas cells transduced with the P2A-based construct resulted in a significantly higher co-expression efficiency of 33.3% (range of 25.9-38.3). Thus, the data in FIG. 5 establish the suitability of the P2A-based bi-cistronic system for efficient co-expression of CAR and the B cell follicle-homing chemokine receptor CXCR5, and its superiority over the IRES-based system.

Figure 6C:
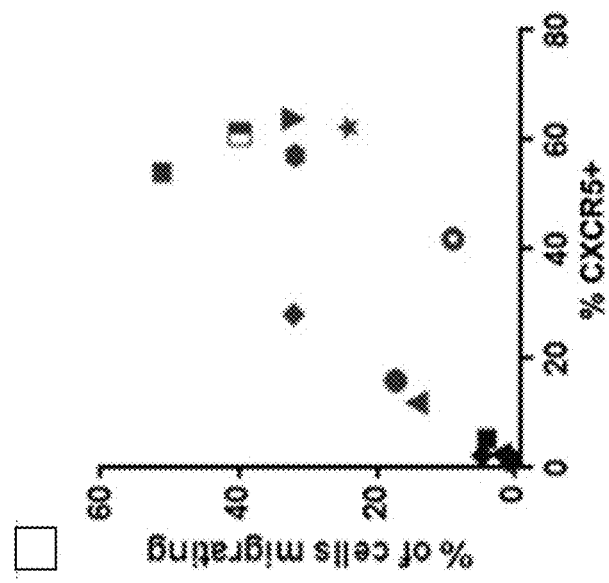
FIG. 6A-FIG. 6C are graphs showing that co-expression of CXCR5 promotes selective migration of chimeric antigen receptor (CAR)-T cells toward CXCL13 in vitro. The percentage of CAR- or CAR/CXCR5-transduced PBMC that migrated toward (FIG. 6A) CXCL12 (SDF-1) or (FIG. 6B) CXCL13 was measured in transwell plates.
Figure 6B:
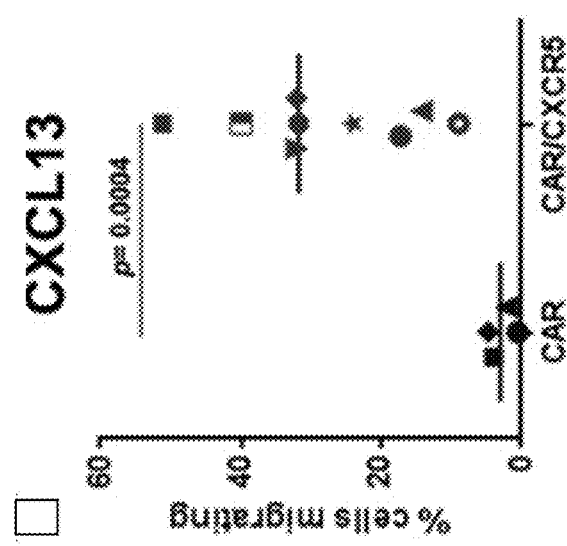
Figure 6A:
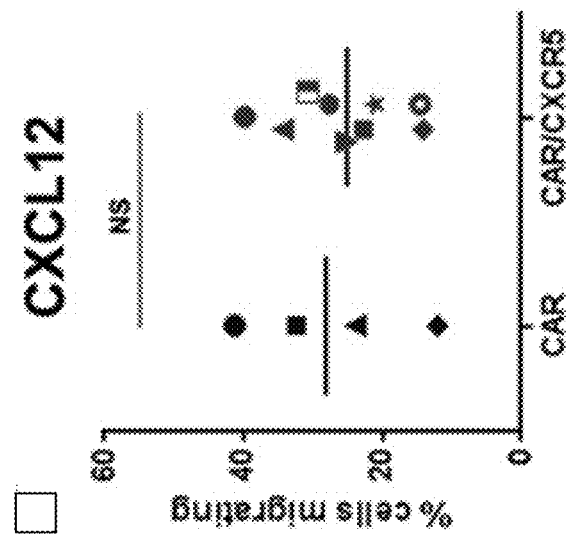

Example 13—CXCR5 Co-Expression Promotes CAR-T Cell Migration Selectively to CXCL13 In Vitro The ability of CXCR5 co-expression to promote migration of CAR-T cells toward CXCL13, the chemokine ligand for CXCR5, was next tested. To this end, an in vitro transwell migration assay was utilized. Using this assay, it was found that both CAR-transduced and CAR/CXCR5-transduced PBMCs similarly migrated toward a positive control chemokine CXCL12 (SDF-1 alpha) that is strongly chemotactic for lymphocytes (Bleul et al., 1996, 184:1101-9), demonstrating the ability of both CAR and CAR/CXCR5-transduced cells to migrate to a chemotactic stimulus (FIG. 6A). In contrast, significantly more CAR/CXCR5-transduced than CAR-transduced PBMCs migrated toward CXCL13 (FIG. 6B). Furthermore, increasing specific migration to CXCL13 was seen with an increase in the percentage of cells expressing CXCR5 (FIG. 6C). For these studies, a median of 54% (range 12-64%) of CAR/CXCR5-transduced cells expressed CXCR5. By contrast, a median of only 2% (range 1-5%) of the CAR-transduced cells expressed CXCR5 and they showed minimal migration to the stimulus. These results demonstrate that co-expression of CXCR5 promotes selective migration of the CAR-T cells toward CXCL13 in vitro.

Figure 7A:
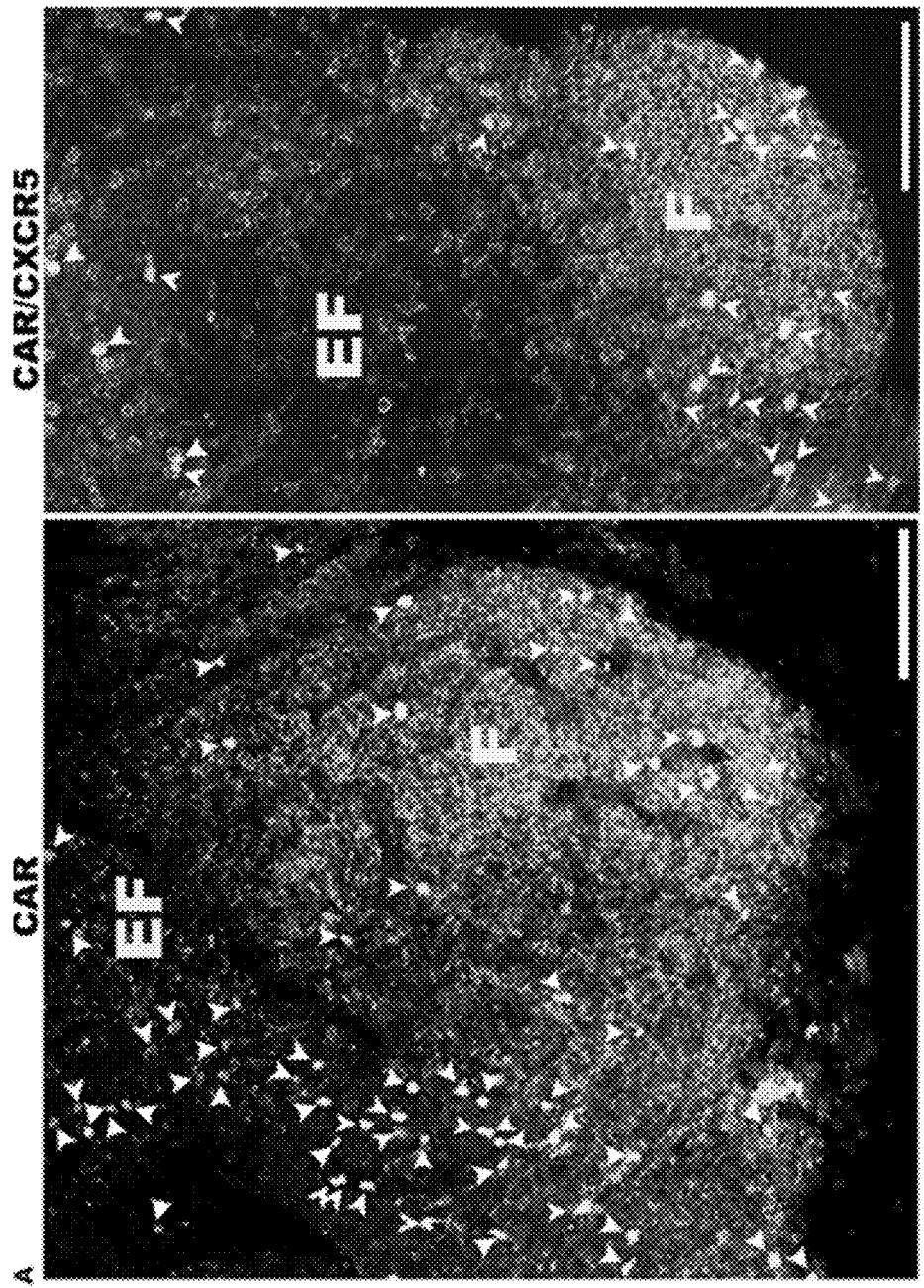
FIG. 7A are images showing that CXCR5 co-expression enhances CD8+ CAR-T cell migration to B cell follicles ex vivo.
Figures 7B, 7C, 7D, 7E, 7F:
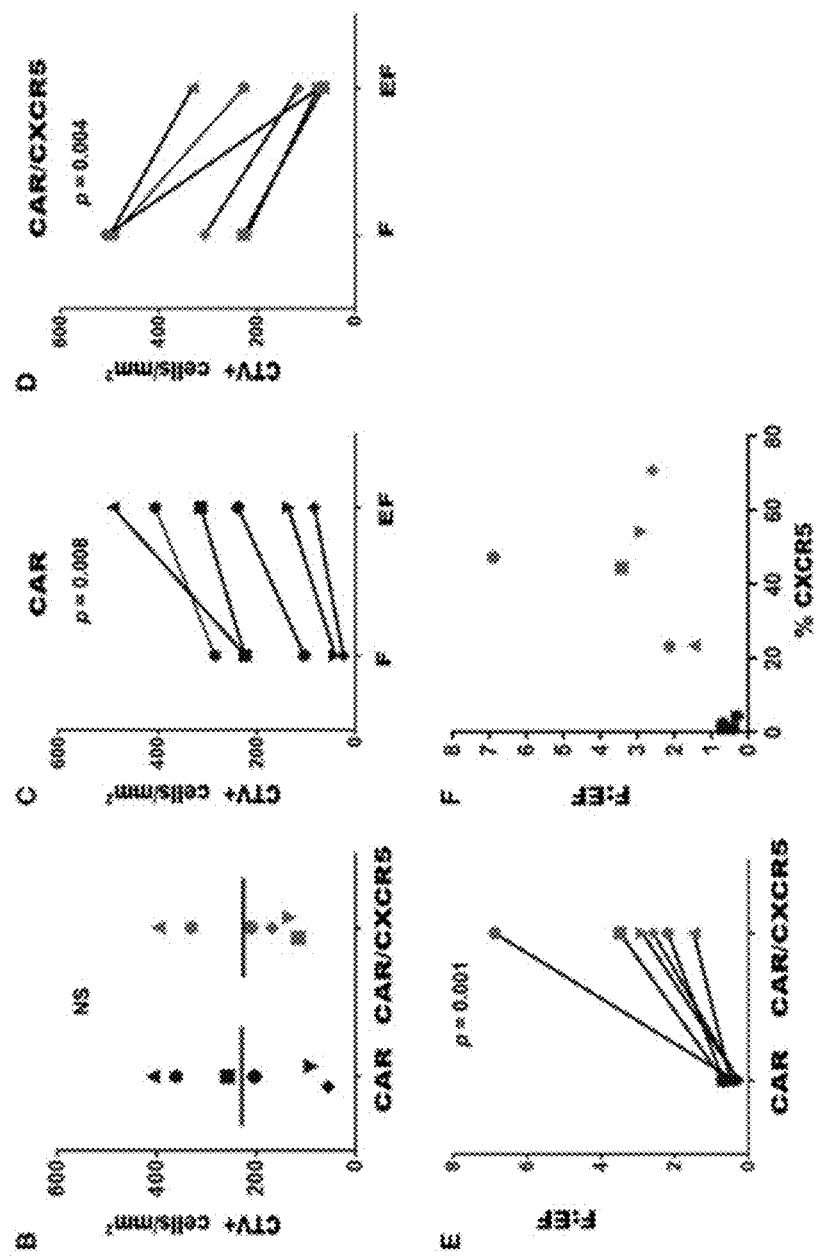
FIG. 7B-FIG. 7F shows the experimental data demonstrating that CXCR5 co-expression enhances CD8+ CAR-T cell migration to B cell follicles ex vivo. Panel B shows similar total levels of CFSE-labeled CD8+ T cells were detected in tissues incubated with CAR- and CAR/CXCR5-transduced cells. Panel C demonstrates that CAR-transduced cells showed higher levels in the extrafollicular regions than in the follicles. Panel D demonstrates that, by contrast, CAR/CXCR5-transduced cells showed increased levels within B cell follicles. Panel E demonstrates that CAR/CXCR5-transduced cells showed higher F:EF ratios compared to CAR-transduced cells. Panel F shows the relationship between the percentage of transduced cells that expressed CXCR5 and F:EF ratios. Each symbol represents individual animals from which CD8+ T cells were derived.

Example 14—CAR/CXCR5-Transduced CD8+ T Cells Selectively Migrate into B Cell Follicles Ex Vivo As an additional means to evaluate the ability of CXCR5 to promote selective migration of CAR-T cells, a novel ex vivo B cell follicle migration assay was developed. This method was adapted from previously described ex vivo live tissue migration assays that tracked T cells in mouse thymus tissue using two-photon microscopy (Melichar et al., 2013, Sci. Signal, 6:ra92; Dzhagalov et al., 2013, PLoS Biol, 11:e1001566). For these studies, the migration of CTV-labeled CAR- and CAR/CXCR5-transduced primary rhesus macaque CD8+ T cells were evaluated in fresh lymph node tissue sections. FIG. 7A shows representative images of sections incubated with CTV-labeled CAR and CAR/CXCR5-transduced cells. Similar levels of total CTV+ cells were detected in lymph node sections incubated with CAR versus CAR/CXCR5-transduced cells (FIG. 7B). While total numbers of cells were similar, significant differences were observed in the levels of CAR- compared to CAR/CXCR5-transduced cells in follicular and extrafollicular compartments. Significantly lower levels of CTV+ cells were found in follicular compared to extrafollicular areas in sections incubated with CAR-transduced cells (FIG. 7C). In contrast, significantly higher levels of CTV+ cells were found in follicular compared to extrafollicular areas in sections incubated with CAR/CXCR5-transduced cells (FIG. 7D). As a result, significantly large increases in the follicular to extrafollicular ratios (F:EF) of CTV-labeled cells were detected in the tissue sections incubated with CAR/CXCR5- compared to CAR-transduced T cells. Sections incubated with CAR/CXCR5-transduced cells showed a median F:EF ratio of 2.8 (range of 1.5-6.9), whereas sections incubated with CAR-transduced T cells showed a median ratio of 0.4 (range 0.3-0.7) (FIG. 7E). An increased follicular to extrafollicular ratio was seen with an increase in the percentage of cells expressing CXCR5 (FIG. 7F). A median of 46% (range 23-71%) of CAR/CXCR5-transduced cells expressed CXCR5 and showed relatively high F:EF ratios. By contrast, a median of only 1.6% (range 0.2-4.1%) of the CAR-transduced cells expressed CXCR5 and showed correspondingly low F:EF ratios. Thus, in this novel ex vivo B cell follicle migration assay, CAR/CXCR5- but not CAR-transduced CD8+ T cells preferentially migrated to B cell follicles.

Figure 8:
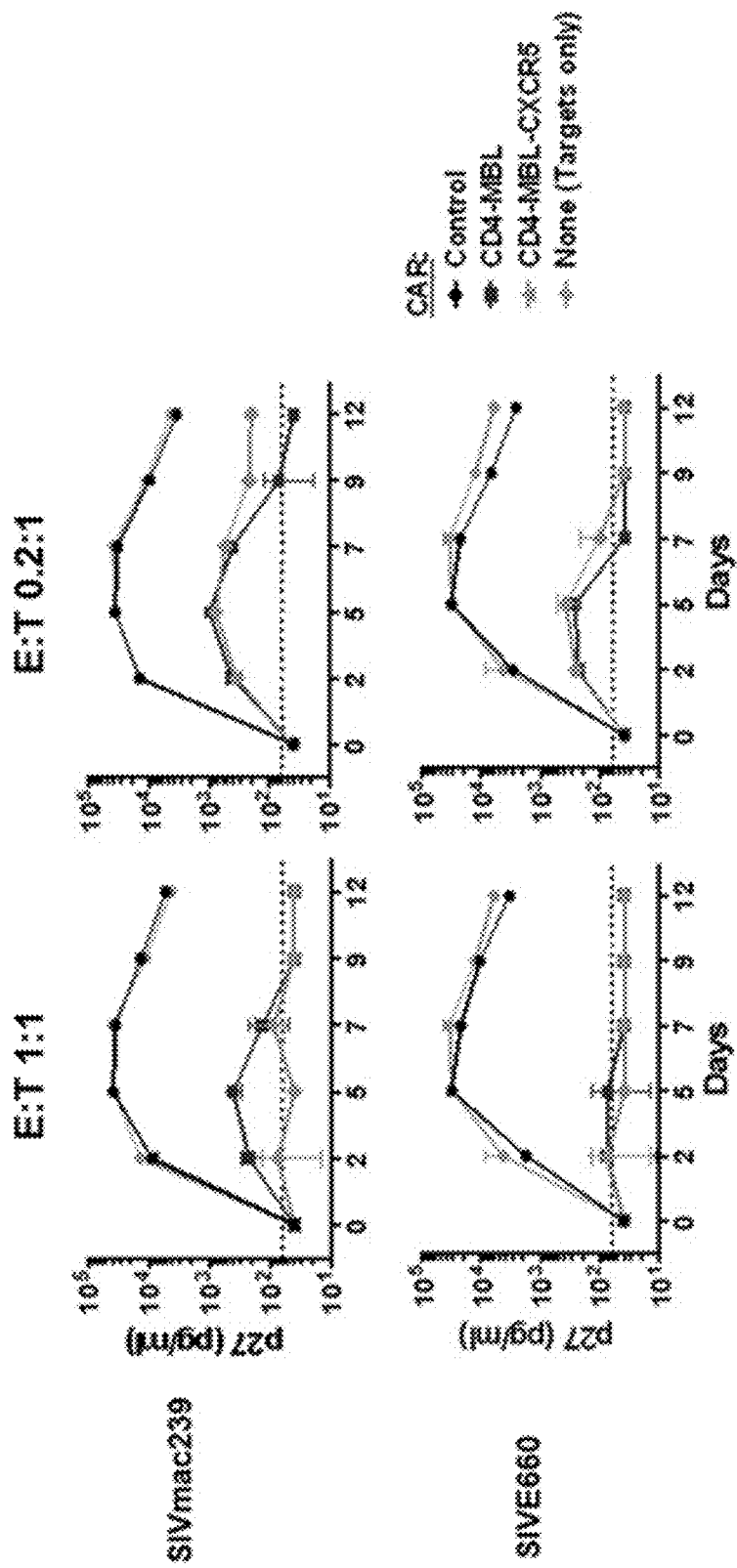
FIG. 8 are graphs showing that chimeric antigen receptor (CAR)/CXCR5-transduced T cells suppress simian immunodeficiency virus (SIV) in vitro. PBMC target cells were infected with the indicated SIVmac239 (top row) and SIVE660 (bottom row) isolates for 24 h. The cells were then washed and mixed with the effector cells transduced as indicated, at effector-to-target ratios (E:T) of 1:1 (left panels) or 0.2:1 (right panels). Culture supernatants were collected on the indicated days, and the presence of virus was determined by p27 ELISA. The effector cells were transduced either with the CD4-mannose-binding lectin (MBL)-CAR alone or CD4-MBL-CAR plus CXCR5. As negative controls, no effector cells, or cells transduced with the negative control 139 CAR were used.

Example 15-CXCR5 Co-Expression Does Not Impair CAR-T Cell-Mediated Suppression of SIV Replication In Vitro The all-rhesus CD4-MBL CAR (rhCD4-MBL) displayed potent suppression of multiple SIV strains. For this study, it was examined whether co-expression of CXCR5 affected the potency of SIV suppression by T cells expressing the rhesus CD4-MBL CAR. PBMCs transduced with the CAR or CAR/CXCR5 vectors, were co-cultured with rhesus PBMC targets infected with two different pathogenic SIV isolates, SIVmac239 and SIVE660. The negative controls employed included adding no effector T cells, and adding effector T cells that were transduced with the 139 CAR that recognizes an irrelevant epitope (a glioma-specific variant of the epidermal growth factor receptor (Morgan et al., 2012, Hum. Gene Ther., 23:1043-53)). Robust spreading of viral infection by both SIV strains was evident in the presence of the negative control effector cells (no effector T cells and 139 CAR-transduced T cells). In contrast, CAR-transduced and CAR/CXCR5-transduced effectors suppressed infection by both strains with equivalent high potency over the 12-day infection, at E:T ratios of 1:1 or 0.2:1 (FIG. 8). These data demonstrate that the antiviral activity of CAR-T cells is not altered by co-expression of the CXCR5 follicular trafficking chemokine receptor on the effector cell surface.

Part C—Nine Day Transduction and Expansion Protocol

Example 16—Retroviral Vector Production

Gamma-retroviruses were generated for expression of CAR and/or CXCR5 in rhesus macaque T cells. Lipofectamine 2000 (Invitrogen)-mediated transfection was carried out using CAR, CXCR5 or CAR P2A CXCR5 pMSGV plasmids as well as the plasmid pBS-CMV-gagpol (a gift from Dr. Patrick Salmon, Addgene plasmid #35614), a plasmid encoding RD114 envelope glycoprotein, and the plasmid pMD.G encoding VSV-G envelope (a gift from Dr. Scott McIvor) at ratios of 3:1:1:0.4, respectively. Retroviral vector supernatants were collected 48 hours after transfection and centrifuged to remove debris.

Lentivirus preparations were generated using pCL20cSLFR MSCV transfer plasmid as well as pCAG-SIVgprre (gag/pol), pMDG (VSV-G envelope) and pCAG4-RTR-SIV (tat/rev) at a ratio of 1:0.6:0.2:0.2 using lipofectamine-mediated transfection. Media was exchanged after 18 hr. Viral supernatants were collected 48 hr later and centrifuged to remove debris. All virus preparations were snap frozen and stored at −80° C. Functional titer was determined by transducing HEK293T cells with the virus.

Example 17—Activation and Transduction of Rhesus T Cells

Primary rhesus macaque PBMC were activated for 2 days in 6 well plates with plate-bound anti-CD3 (FN18) and soluble anti-CD28.2 (both from NHP Reagent Resource) in X-Vivo 15 completed with 10% heat inactivated FBS, 100 U/ml penicillin, 100 g/ml streptomycin, 2 mM glutamine, and 50 IU/ml IL-2. For PBMC activated with CD3 and CD28 antibodies, the population becomes highly enriched for T cells. RetroNectin (TaKaRa)-mediated transduction was carried out on the activated T cells with the gamma-retrovirus at an MOI of 0.5. After coating 6 well plates with Retronectin, retroviral vector supernatants, diluted in serum-free media, were added and centrifuged for 2 hours at 2000×g to facilitate binding of the retrovirus. After removal of the unbound retrovirus, activated PBMC (1.5×10E6 cells/well) were added to the retrovirus-coated wells and centrifuged at 1000×g for 10 minutes. Mock-transduced cells were subjected to exactly the same procedures without the addition of retrovirus to the RetroNectin-coated wells. Cells were cultivated for 2 days prior to analysis by flow cytometry.

Example 18—Expansion of Transduced Rhesus T Cells

Two days post transduction, cells were seeded in a G-Rex 6 well plate (Wilson Wolf) at a density of 1×10E6 cells/cm² in 30 ml of X-Vivo 15 completed with 10% heat inactivated FBS, 100 U/ml penicillin, 100 g/ml streptomycin, 2 mM glutamine, and 50 M beta-mercaptoethanol, and 50 IU/ml IL-2. Cells were grown undisturbed for 4 days before collection and analysis by flow cytometry.

Example 19-CTV Staining of Transduced Cells

Cells were stained with the Cell Trace Violet Cell Proliferation kit (Invitrogen). Briefly, cells were placed in aliquots of 60×10E6 cells suspended in PBS containing 10% FBS. Cell Trace Violet, diluted in PBS, was added to a final concentration of 5.5 M and cells were incubated for 15 min at 37° C. The reaction was stopped with a 5 min incubation in 5 times the reaction volume of complete media. Cells were centrifuged and re-suspended in complete medium and allowed to rest for 10 minutes before use.

Example 20 Flow Cytometry

Cells were analyzed using a CytoFLEX flow cytometer (Beckman Coulter). For the 6 color standard panel, the following antibodies were used: CD4 (M-T477, reactive with endogenous rhCD4 and the rhCD4-MBL CAR), CD3 (SP34-2), CD8 (RPA-T8) (all from BD Bioscience), CXCR5 (MUSUBEE) (eBioscience), MBL2 (3E7) (Invitrogen).

Viability was assessed with the Live/Dead Fixable Near IR Dead Cell Stain Kit (Invitrogen). For the 11 color panel, the following antibodies were used in addition to CTV and the Live/Dead stain: CD4 (M-T477), CD3 (SP34-2), CD8 (RPA-T8), CCR7 (150503), CD28 (CD28.2), CD95(DX2) (all from BD Bioscience), CXCR5 (MUSUBEE) (eBioscience), MBL2 (3E7) (Invitrogen), CD159a (Z199) (Beckman Coulter). A minimum of 70,000 events were acquired for each sample. Data analysis utilized FlowJo v10 (FlowJo, LLC).

Example 21—Results

Methods have been developed that allow transduction (e.g., for CAR and CXCR5 co-expression) and expansion of cells in 9 days while maintaining viability and ~30% central memory T cells (TCM) (less differentiated memory cells). Most other methods of transducing and expanding cells take weeks, so the methods described herein represent a significant improvement in time without any apparent loss of quality. Rhesus macaque CD4-MBL-CAR/CXCR5 T cells were used herein, but the methods could be applied to cells from other species using similar but species-specific vectors.

Rhesus macaque PBMCs were transduced with CAR and CXCR5 and expanded in 9 days. Flow cytometric analysis of cells sorted on live, singlet, CD3 T cells co-labeled with MBL antibodies, which bind CD4-MBL-CAR, and CXCR5 antibodies is shown in FIG. 9.

The 9-day procedure described herein yields sufficient cell numbers for cellular immunotherapy (FIG. 10). This procedure was used to yield 10E8 cells/kg for treatment of an SIV-infected macaque. These experiments also demonstrated that co-expression (FIG. 11) and viability (FIG. 12) was maintained after expansion.

Central memory T cells (TCM) were maintained after 9 day transduction and expansion (FIG. 13). CD4-MBL-CAR/CXCR5 transduced cells were produced with the 9 day protocol. Briefly, rhesus PBMC were stimulated with anti CD3/anti CD28 beads or with plate bound anti CD3 and soluble anti CD28 for two days, subjected to one round of transduction with CAR/CXCR5 retrovirus and then expanded for 4 days in the GREX plate in 50 U/ml IL-2, 50 µM beta mercaptoethanol. Cells were cryopreserved on d9, thawed and used immediately in flow cytometry. Gating strategy: Lymphocytes, singlets, live cells, CD3+, CD8+ for total cells or lymphocytes, singlets, live cells, CD3+, MBL+, CD8+ for transduced cells. Phenotype definitions: CM defined as CD95+, CD28+, CCR7+; EM1 defined as CD95+, CD28+, CCR7−; EM2 defined as CD95+, CD28−, CCR7−.

An SIV infected animal was treated with CD4-MBL-CAR/CXCR5 T cells labeled with a live cell stain (CTV) and the animal was sacrificed two days later and the localization of the labeled cells evaluated. CTV-labeled cells were detected in spleen, lymph nodes, liver, and very few in lung. In the spleen and lymph nodes, CTV-labeled cells were detected in B cell follicles. Clusters of CTV+ cells were detected in the T cell zones, likely proliferating (a site that T cells normally undergo expansion). These data also indicate that 9 day transduction and expansion protocol described herein does not lead to transduced cells accumulating in the lung, which is an ongoing problem.

FIG. 14 shows that CTV-labeled CD4-CD3-CAR/CXCR5-transduced PBMCs (pseudo-colored red and indicated with arrow heads) were located inside B cell follicles of spleen (left) and LN (middle) but not in lung (right). Sections were stained with either IgM antibodies or anti-CD20 antibodies to label B cells and identify follicles (F).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of preparing a cellular composition for suppressing replication of HIV in B cell follicles in a subject having HIV, comprising:

providing peripheral blood mononuclear cells from the subject having HIV;

transducing the cells with a vector comprising a HIV-based CAR construct and a nucleic acid molecule encoding a CXCR5 polypeptide as shown in SEQ ID NO: 5;

culturing the transduced cells, and infusing the cultured transduced cells into the subject, wherein the cultured transduced cells migrate to B cell follicles and suppress replication of HIV in B cell follicles to reduce levels of HIV in the subject in the absence of anti-viral HIV drugs relative to HIV levels in the subject prior to the infusing step.

2. The method of claim 1, further comprising monitoring the subject for the presence of HIV.

3. The method of claim 1, further comprising monitoring the subject for the amount of HIV.

4. The method of claim 1, further comprising obtaining the cells from the subject using apheresis.

5. The method of claim 1, wherein the HIV-based CAR construct comprises the sequence shown in SEQ ID NO: 6, 8, or 10.

6. The method of claim 1, wherein the HIV-based CAR construct is encoded by a nucleic acid having the sequence shown in SEQ ID NO: 7, 9, or 11.

7. The method of claim 1, wherein the vector is a lentiviral vector or a gamma retroviral vector.

8. The method of claim 1, wherein the transducing step comprises gene editing.

9. The method of claim 8, wherein the gene editing comprises CRISPR or TALEN.

10. A method of suppressing replication of HIV in B cell follicles in a subject having HIV, comprising:

providing peripheral blood mononuclear cells from the subject having HIV;

transducing the cells with a vector comprising a HIV-based CAR construct and a nucleic acid molecule encoding a CXCR5 polypeptide as shown in SEQ ID NO: 5, wherein the HIV-based CAR construct comprises an antigen-binding targeting portion that recognizes gp120 and/or gp41;

culturing the transduced cells, and infusing the cultured transduced cells into the subject, wherein the cultured transduced cells migrate to B cell follicles, thereby suppressing replication of HIV in B cell follicles to reduce levels of HIV in the subject in the absence of anti-viral HIV drugs relative to HIV levels in the subject prior to the infusing step.

11. A method of suppressing replication of HIV in B cell follicles in a subject having HIV, comprising:
- providing peripheral blood mononuclear cells from the subject having HIV;
- transducing the cells with a vector comprising a HIV-based CAR construct and a codon-optimized nucleic acid molecule encoding a CXCR5 polypeptide as shown in SEQ ID NO: 5; wherein the HIV-based CAR construct comprises an antigen-binding targeting portion that recognizes gp120 and/or gp41; and
- culturing the transduced cells,
- infusing the cultured transduced cells into the subject, wherein the cultured transduced cells migrate to B cell follicles, thereby suppressing replication of HIV in B cell follicles to reduce levels of HIV in the subject in the absence of anti-viral HIV drugs relative to HIV levels in the subject prior to the infusing step.

* * * * *

SEQUENCE LISTING

```
<160> NUMBER OF SEQ ID NOS: 11

<210> SEQ ID NO 1
<211> LENGTH: 372
<212> TYPE: PRT
<213> ORGANISM: Homo sapiens

<400> SEQUENCE: 1

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
                20                  25                  30

Val Glu Asn His Leu Cys Pro Ala Thr Glu Gly Pro Leu Met Ala Ser
            35                  40                  45
```

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
                100                 105                 110

Val Gly Trp Val Leu Gly Thr Phe Leu Cys Lys Thr Val Ile Ala Leu
            115                 120                 125

His Lys Val Asn Phe Tyr Cys Ser Ser Leu Leu Leu Ala Cys Ile Ala
130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
                180                 185                 190

Gly His His Asn Asn Ser Leu Pro Arg Cys Thr Phe Ser Gln Glu Asn
            195                 200                 205

Gln Ala Glu Thr His Ala Trp Phe Thr Ser Arg Phe Leu Tyr His Val
210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
                260                 265                 270

Ser Pro Tyr His Ile Val Ile Phe Leu Asp Thr Leu Ala Arg Leu Lys
            275                 280                 285

Ala Val Asp Asn Thr Cys Lys Leu Asn Gly Ser Leu Pro Val Ala Ile
290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
                340                 345                 350

Pro Ser Trp Arg Arg Ser Ser Leu Ser Glu Ser Glu Asn Ala Thr Ser
            355                 360                 365

Leu Thr Thr Phe
    370

<210> SEQ ID NO 2
<211> LENGTH: 2919
<212> TYPE: DNA
<213> ORGANISM: Homo sapiens

<400> SEQUENCE: 2
aaaaaaaaaa agtgatgagt tgtgaggcag gtcgcggccc tactgcctca ggagacgatg      60
cgcagctcat ttgcttaaat ttgcagctga cggctgccac ctctctagag gcacctggcg     120
gggagcctct caacataaga cagtgaccag tctggtgact cacagccggc acagccatga     180
actacccgct aacgctggaa atggacctcg agaacctgga ggacctgttc tgggaactgg     240

```
acagattgga caactataac gacacctccc tggtggaaaa tcatctctgc cctgccacag    300
agggcccct  catggcctcc ttcaaggccg tgttcgtgcc cgtggcctac agcctcatct    360
tcctcctggg cgtgatcggc aacgtcctgg tgctggtgat cctggagcgg caccggcaga    420
cacgcagttc cacggagacc ttcctgttcc acctggccgt ggccgacctc ctgctggtct    480
tcatcttgcc ctttgccgtg gccgagggct ctgtgggctg ggtcctgggg accttcctct    540
gcaaaactgt gattgccctg cacaaagtca acttctactg cagcagcctg ctcctggcct    600
gcatcgccgt ggaccgctac ctggccattg tccacgccgt ccatgcctac cgccaccgcc    660
gcctcctctc catccacatc acctgtggga ccatctggct ggtgggcttc tccttgcct     720
tgccagagat tctcttcgcc aaagtcagcc aaggccatca caacaactcc ctgccacgtt    780
gcaccttctc caagagaaac caagcagaaa cgcatgcctg gttcacctcc cgattcctct    840
accatgtggc gggattcctg ctgcccatgc tggtgatggg ctggtgctac gtggggtag    900
tgcacaggtt gcgccaggcc cagcggcgcc ctcagcggca aaggcagtc agggtggcca    960
tcctggtgac aagcatcttc ttcctctgct ggtcacccta ccacatcgtc atcttcctgg    1020
acaccctggc gaggctgaag gccgtggaca taccctgcaa gctgaatggc tctctccccg    1080
tggccatcac catgtgtgag ttcctgggcc tggcccactg ctgcctcaac ccatgctct    1140
acactttcgc cggcgtgaag ttccgcagtg acctgtcgcg gctcctgacg aagctgggct    1200
gtaccggccc tgcctcccctg tgccagtctct cccctagctg gcgcaggagc agtctctctg   1260
agtcagagaa tgccacctct ctcaccacgt tctaggtccc agtgtcccct tttattgctg    1320
cttttccttg gggcaggcag tgatgctgga tgctccttcc aacaggagct gggatcctaa    1380
ggctcaccg tggctaagag tgtcctagga gtatcctcat ttggggtagc tagaggaacc    1440
aacccccatt tctagaacat ccctgccagc tcttctgccg gccctgggc taggctggag    1500
cccagggagc ggaaagcagc tcaaaggcac agtgaaggct gtccttaccc atctgcaccc    1560
ccctgggctg agagaacctc acgcacctcc catcctaatc atccaatgct caagaaacaa    1620
cttctacttc tgcccttgcc aacggagagc gcctgccct cccagaacac actccatcag    1680
cttaggggct gctgacctcc acagcttccc ctctctcctc ctgcccacct gtcaaacaaa    1740
gccagaagct gagcaccagg ggatgagtgg aggttaaggc tgaggaaagg ccagctggca    1800
gcagagtgtg gccttcggac aactcagtcc ctaaaaacac agacattctg ccaggcccccc  1860
aagcctgcag tcatcttgac caagcaggaa gctcagactg gttgagttca ggtagctgcc    1920
cctggctctg accgaaacag cgctgggtcc accccatgtc accggatcct gggtggtctg    1980
caggcagggc tgactctagg tgcccttgga ggccagccag tgacctgagg aagcgtgaag    2040
gccgagaagc aagaaagaaa cccgacagag ggaagaaaag agctttcttc ccgaacccca    2100
aggagggaga tggatcaatc aaacccggcg gtccctccg ccaggcgaga tggggtgggg    2160
tggaaactc ctagggtggc tgggtccagg ggatgggagg ttgtgggcat tgatgggaa     2220
ggaggctggc ttgtccctc ctcactccct tcccataagc tatagacccg aggaaactca   2280
gagtcggaac ggagaaaggt ggactggaag gggcccgtgg gagtcatctc aaccatcccc    2340
tccgtggcat caccttaggc agggaagtgt aagaaacaca ctgaggcagg gaagtcccca    2400
ggccccagga agccgtgccc tgccccgtg aggatgtcac tcagatggaa ccgcaggaag    2460
ctgctccgtg cttgtttgct cacctggggt gtgggaggcc cgtccggcag ttctgggtgc    2520
tccctaccac ctccccagcc tttgatcagg tgggagtca gggaccctg ccctttgtccc    2580
actcaagcca agcagccaag ctccttggga ggccccactg gggaaataac agctgtggct    2640
```

```
cacgtgagag tgtcttcacg gcaggacaac gaggaagccc taagacgtcc cttttttctc      2700
tgagtatctc ctcgcaagct gggtaatcga tggggagtc tgaagcagat gcaaagaggc       2760
aagaggctgg attttgaatt ttcttttta taaaaaggca cctataaaac aggtcaatac       2820
agtacaggca gcacagagac ccccggaaca agcctaaaaa ttgtttcaaa ataaaaacca     2880
agaagatgtc ttcacatatt gtaaaaaaaa aaaaaaaa                              2919
```

<210> SEQ ID NO 3
<211> LENGTH: 327
<212> TYPE: PRT
<213> ORGANISM: Homo sapiens

<400> SEQUENCE: 3

```
Met Ala Ser Phe Lys Ala Val Phe Val Pro Val Ala Tyr Ser Leu Ile
1               5                   10                  15

Phe Leu Leu Gly Val Ile Gly Asn Val Leu Val Leu Val Ile Leu Glu
                20                  25                  30

Arg His Arg Gln Thr Arg Ser Ser Thr Glu Thr Phe Leu Phe His Leu
            35                  40                  45

Ala Val Ala Asp Leu Leu Leu Val Phe Ile Leu Pro Phe Ala Val Ala
        50                  55                  60

Glu Gly Ser Val Gly Trp Val Leu Gly Thr Phe Leu Cys Lys Thr Val
65                  70                  75                  80

Ile Ala Leu His Lys Val Asn Phe Tyr Cys Ser Ser Leu Leu Leu Ala
                85                  90                  95

Cys Ile Ala Val Asp Arg Tyr Leu Ala Ile Val His Ala Val His Ala
            100                 105                 110

Tyr Arg His Arg Arg Leu Leu Ser Ile His Ile Thr Cys Gly Thr Ile
        115                 120                 125

Trp Leu Val Gly Phe Leu Leu Ala Leu Pro Glu Ile Leu Phe Ala Lys
130                 135                 140

Val Ser Gln Gly His His Asn Asn Ser Leu Pro Arg Cys Thr Phe Ser
145                 150                 155                 160

Gln Glu Asn Gln Ala Glu Thr His Ala Trp Phe Thr Ser Arg Phe Leu
                165                 170                 175

Tyr His Val Ala Gly Phe Leu Leu Pro Met Leu Val Met Gly Trp Cys
            180                 185                 190

Tyr Val Gly Val Val His Arg Leu Arg Gln Ala Gln Arg Arg Pro Gln
        195                 200                 205

Arg Gln Lys Ala Val Arg Val Ala Ile Leu Val Thr Ser Ile Phe Phe
210                 215                 220

Leu Cys Trp Ser Pro Tyr His Ile Val Ile Phe Leu Asp Thr Leu Ala
225                 230                 235                 240

Arg Leu Lys Ala Val Asp Asn Thr Cys Lys Leu Asn Gly Ser Leu Pro
                245                 250                 255

Val Ala Ile Thr Met Cys Glu Phe Leu Gly Leu Ala His Cys Cys Leu
            260                 265                 270

Asn Pro Met Leu Tyr Thr Phe Ala Gly Val Lys Phe Arg Ser Asp Leu
        275                 280                 285

Ser Arg Leu Leu Thr Lys Leu Gly Cys Thr Gly Pro Ala Ser Leu Cys
    290                 295                 300

Gln Leu Phe Pro Ser Trp Arg Arg Ser Ser Leu Ser Glu Ser Glu Asn
305                 310                 315                 320
```

Ala Thr Ser Leu Thr Thr Phe
            325

<210> SEQ ID NO 4
<211> LENGTH: 2896
<212> TYPE: DNA
<213> ORGANISM: Homo sapiens

<400> SEQUENCE: 4

| | | | | | |
|---|---|---|---|---|---|
| ccactctaag | gaatgcggtc | cctttgacag | gcgaaaaact | gaagttggaa | aagacaaagt | 60 |
| gatttgttca | aaattgaaat | ttgaaacttg | acatttggtc | agtgggccct | atgtaggaaa | 120 |
| aaacctccaa | gagagctagg | gttcctctca | gagaggaaag | acaggtcctt | aggtcctcac | 180 |
| cctcccgtct | ccttgccctt | gcagttctgg | gaactggaca | gattggacaa | ctataacgac | 240 |
| acctccctgg | tggaaaatca | tctctgccct | gccacagagg | ggcccctcat | ggcctccttc | 300 |
| aaggccgtgt | tcgtgcccgt | ggcctacagc | ctcatcttcc | tcctgggcgt | gatcggcaac | 360 |
| gtcctggtgc | tggtgatcct | ggagcggcac | cggcagacac | gcagttccac | ggagaccttc | 420 |
| ctgttccacc | tggccgtggc | cgacctcctg | ctggtcttca | tcttgccctt | tgccgtggcc | 480 |
| gagggctctg | tgggctgggt | cctggggacc | ttcctctgca | aaactgtgat | tgccctgcac | 540 |
| aaagtcaact | tctactgcag | cagcctgctc | ctggcctgca | tcgccgtgga | ccgctacctg | 600 |
| gccattgtcc | acgccgtcca | tgcctaccgc | accgccgcc | cctctccat | ccacatcacc | 660 |
| tgtgggacca | tctggctggt | gggcttcctc | cttgccttgc | cagagattct | cttcgccaaa | 720 |
| gtcagccaag | gccatcacaa | caactccctg | ccacgttgca | ccttctccca | agagaaccaa | 780 |
| gcagaaacgc | atgcctggtt | cacctcccga | ttcctctacc | atgtggcggg | attcctgctg | 840 |
| cccatgctgg | tgatgggctg | tgctacgtg | ggggtagtgc | acaggttgcg | ccaggcccag | 900 |
| cggcgccctc | agcggcagaa | ggcagtcagg | gtggccatcc | tggtgacaag | catcttcttc | 960 |
| ctctgctggt | caccctacca | catcgtcatc | ttcctggaca | ccctggcgag | gctgaaggcc | 1020 |
| gtggacaata | cctgcaagct | gaatggctct | ctccccgtgg | ccatcaccat | gtgtgagttc | 1080 |
| ctgggcctgg | cccactgctg | cctcaacccc | atgctctaca | cttttcgccgg | cgtgaagttc | 1140 |
| cgcagtgacc | tgtcgcggct | cctgacgaag | ctgggctgta | ccggccctgc | ctccctgtgc | 1200 |
| cagctcttcc | ctagctggcg | caggagcagt | ctctctgagt | cagagaatgc | cacctctctc | 1260 |
| accacgttct | aggtcccagt | gtccccttt | attgctgctt | ttccttgggg | caggcagtga | 1320 |
| tgctggatgc | tccttccaac | aggagctggg | atcctaaggg | ctcaccgtgg | ctaagagtgt | 1380 |
| cctaggagta | tcctcatttg | gggtagctag | aggaaccaac | ccccatttct | agaacatccc | 1440 |
| tgccagctct | tctgccggcc | ctggggctag | gctggagccc | agggagcgga | aagcagctca | 1500 |
| aaggcacagt | gaaggctgtc | cttacccatc | tgcaccccc | tgggctgaga | gaacctcacg | 1560 |
| cacctcccat | cctaatcatc | caatgctcaa | gaaacaactt | ctacttctgc | ccttgccaac | 1620 |
| ggagagcgcc | tgcccctccc | agaacacact | ccatcagctt | aggggctgct | gacctccaca | 1680 |
| gcttccccctc | tctcctcctg | cccacctgtc | aaacaaagcc | agaagctgag | caccagggga | 1740 |
| tgagtggagg | ttaaggctga | ggaaaggcca | gctggcagca | gagtgtggcc | ttcggacaac | 1800 |
| tcagtcccta | aaaacacaga | cattctgcca | ggcccccaag | cctgcagtca | tcttgaccaa | 1860 |
| gcaggaagct | cagactggtt | gagttcaggt | agctgcccct | ggctctgacc | gaaacagcgc | 1920 |
| tgggtccacc | ccatgtcacc | ggatcctggg | tggtctgcag | gcaggctga | ctctaggtgc | 1980 |
| ccttggaggc | cagccagtga | cctgaggaag | cgtgaaggcc | gagaagcaag | aaagaaaccc | 2040 |

```
gacagaggga agaaaagagc tttcttcccg aaccccaagg agggagatgg atcaatcaaa    2100
cccggcggtc ccctccgcca ggcgagatgg ggtggggtgg agaactccta gggtggctgg    2160
gtccagggga tgggaggttg tgggcattga tggggaagga ggctggcttg tccctcctc    2220
actcccttcc cataagctat agacccgagg aaactcagag tcggaacgga gaaaggtgga    2280
ctggaagggg cccgtgggag tcatctcaac catcccctcc gtggcatcac cttaggcagg    2340
gaagtgtaag aaacacactg aggcaggaa gtccccaggc cccaggaagc cgtgccctgc    2400
ccccgtgagg atgtcactca gatggaaccg caggaagctg ctccgtgctt gtttgctcac    2460
ctggggtgtg ggaggcccgt ccggcagttc tgggtgctcc ctaccacctc cccagccttt    2520
gatcaggtgg ggagtcaggg acccctgccc ttgtcccact caagccaagc agccaagctc    2580
cttgggaggc cccactgggg aaataacagc tgtggctcac gtgagagtgt cttcacggca    2640
ggacaacgag gaagccctaa gacgtccctt ttttctctga gtatctcctc gcaagctggg    2700
taatcgatgg gggagtctga agcagatgca aagaggcaag aggctggatt ttgaattttc    2760
ttttttaataa aaaggcacct ataaaacagg tcaatacagt acaggcagca cagagacccc    2820
cggaacaagc ctaaaaattg tttcaaaata aaaaccaaga agatgtcttc acatattgta    2880
aaaaaaaaaa aaaaaa                                                    2896

<210> SEQ ID NO 5
<211> LENGTH: 1119
<212> TYPE: DNA
<213> ORGANISM: Artificial Sequence
<220> FEATURE:
<223> OTHER INFORMATION: Synthetically generated coding sequence

<400> SEQUENCE: 5
atgaactacc ccctgaccct ggagatggac ctggagaacc tggaggacct gttctgggag      60
ctggacagac tggacaacta caatgatacc tccctggtgg agaaccatct gtgccccgcc     120
accgagggcc ccctgatggc cagcttcaag gccgtgttcg tgcccgtggc ctacagcctg     180
atcttcctgc tgggcgtgat cggcaacgtg ctggtgctgg tgatcctgga gagacacaga     240
cagaccagaa gcagcaccga gaccttcctg ttccacctgg ccgtggccga cctgctgctg    300
gtgttcatcc tgcccttcgc cgtggccgag ggcagcgtgg gctgggtgct gggcaccttc    360
ctgtgcaaga ccgtgatcgc cctgcacaag gtgaacttct actgcagcag cctgctgctg    420
gcctgcatcg ccgtggacag atacctggcc atcgtgcacg ccgtgcacgc ctacagacac    480
agaagactgc tgagcatcca catcacctgc ggcaccatct ggctggtggg cttcctgctg    540
gccctgcccg agatcctgtt cgccaaggtg agccagggcc accacaacaa cagcctgccc    600
agatgcacct tcagccagga gaaccaggcc gagacccacg cctggttcac cagcagattc    660
ctgtaccacg tggccggctt cctgctgccc atgctggtga tgggctggtg ctacgtgggc    720
gtggtgcaca cactgagaca ggcccagaga gacccagaa acagaaggc cgtgagagtg    780
gccatcctgg tgaccagcat cttcttcctg tgctggagcc cctaccacat cgtgatcttc    840
ctggacaccc tggccagact gaaggccgtg gacaacacct gcaagctgaa cggcagcctg    900
cccgtggcca tcaccatgtg cgagttcctg ggcctggccc actgctgcct gaaccccatg    960
ctgtacacct tcgccggagt gaagttcaga agcgacctga gcagactgct gaccaagctg   1020
ggctgcaccg cccgccag cctgtgccag ctgttcccca gctggagaag aagcagcctg   1080
agcgagagcg agaacgccac cagcctgacc accttctga                          1119
```

-continued

```
<210> SEQ ID NO 6
<211> LENGTH: 717
<212> TYPE: PRT
<213> ORGANISM: Artificial Sequence
<220> FEATURE:
<223> OTHER INFORMATION: Protein encoded by synthetically generated
      expression cassette

<400> SEQUENCE: 6

Met Val Arg Gly Val Pro Phe Arg His Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
            195                 200                 205

Gly Gly Gly Gly Ser Gly Gly Gly Ser Gly Gly Gly Gly Ser Gly
        210                 215                 220

Gly Gly Ser Gly Gly Gly Ser Gly Gly Gly Ser Gly Gly
225                 230                 235                 240

Gly Gly Ser Gln Val Gln Leu Leu Glu Ser Gly Ala Glu Val Lys Lys
                245                 250                 255

Pro Gly Ser Ser Val Lys Val Ser Cys Lys Ala Ser Gly Asp Thr Phe
            260                 265                 270

Ile Arg Tyr Ser Phe Thr Trp Val Arg Gln Ala Pro Gly Gln Gly Leu
        275                 280                 285

Glu Trp Met Gly Arg Ile Ile Thr Ile Leu Asp Val Ala His Tyr Ala
    290                 295                 300

Pro His Leu Gln Gly Arg Val Thr Ile Thr Ala Asp Lys Ser Thr Ser
305                 310                 315                 320

Thr Val Tyr Leu Glu Leu Arg Asn Leu Arg Ser Asp Asp Thr Ala Val
                325                 330                 335

Tyr Phe Cys Ala Gly Val Tyr Glu Gly Glu Ala Asp Glu Gly Glu Tyr
            340                 345                 350

Asp Asn Asn Gly Phe Leu Lys His Trp Gly Gln Gly Thr Leu Val Thr
        355                 360                 365
```

Val Thr Ser Gly Gly Gly Gly Ser Gly Gly Gly Ser Gly Gly Gly
    370                 375                 380

Gly Ser Glu Leu Glu Leu Thr Gln Ser Pro Ala Thr Leu Ser Val Ser
385                 390                 395                 400

Pro Gly Glu Arg Ala Thr Leu Ser Cys Arg Ala Ser Glu Ser Val Ser
                405                 410                 415

Ser Asp Leu Ala Trp Tyr Gln Gln Lys Pro Gly Gln Ala Pro Arg Leu
            420                 425                 430

Leu Ile Tyr Gly Ala Ser Thr Arg Ala Thr Gly Val Pro Ala Arg Phe
        435                 440                 445

Ser Gly Ser Gly Ser Gly Ala Glu Phe Thr Leu Thr Ile Ser Ser Leu
    450                 455                 460

Gln Ser Glu Asp Phe Ala Val Tyr Tyr Cys Gln Gln Tyr Asn Asn Trp
465                 470                 475                 480

Pro Pro Arg Tyr Thr Phe Gly Gln Gly Thr Arg Leu Glu Ile Lys Ala
                485                 490                 495

Ala Ala Ile Glu Val Met Tyr Pro Pro Tyr Leu Asp Asn Glu Lys
            500                 505                 510

Ser Asn Gly Thr Ile Ile His Val Lys Gly Lys His Leu Cys Pro Ser
    515                 520                 525

Pro Leu Phe Pro Gly Pro Ser Lys Pro Phe Trp Val Leu Val Val Val
530                 535                 540

Gly Gly Val Leu Ala Cys Tyr Ser Leu Leu Val Thr Val Ala Phe Ile
545                 550                 555                 560

Ile Phe Trp Val Arg Ser Lys Arg Ser Arg Leu Leu His Ser Asp Tyr
                565                 570                 575

Met Asn Met Thr Pro Arg Arg Pro Gly Pro Thr Arg Lys His Tyr Gln
            580                 585                 590

Pro Tyr Ala Pro Pro Arg Asp Phe Ala Ala Tyr Arg Ser Arg Val Lys
        595                 600                 605

Phe Ser Arg Ser Ala Asp Ala Pro Ala Tyr Gln Gln Gly Gln Asn Gln
    610                 615                 620

Leu Tyr Asn Glu Leu Asn Leu Gly Arg Arg Glu Glu Tyr Asp Val Leu
625                 630                 635                 640

Asp Lys Arg Arg Gly Arg Asp Pro Glu Met Gly Gly Lys Pro Arg Arg
                645                 650                 655

Lys Asn Pro Gln Glu Gly Leu Tyr Asn Glu Leu Gln Lys Asp Lys Met
            660                 665                 670

Ala Glu Ala Tyr Ser Glu Ile Gly Met Lys Gly Glu Arg Arg Arg Gly
        675                 680                 685

Lys Gly His Asp Gly Leu Tyr Gln Gly Leu Ser Thr Ala Thr Lys Asp
    690                 695                 700

Thr Tyr Asp Ala Leu His Met Gln Ala Leu Pro Pro Arg
705                 710                 715

<210> SEQ ID NO 7
<211> LENGTH: 2154
<212> TYPE: DNA
<213> ORGANISM: Artificial Sequence
<220> FEATURE:
<223> OTHER INFORMATION: Synthetically generated expression cassette

<400> SEQUENCE: 7
atggttcgag gcgtgccctt ccggcatctg ctgctggtgc tgcagctggc tctcctgcct    60
gccgccaccc agggcaagaa agtggtgctg ggcaaaaagg cgacaccgt ggaactgacc    120

| | | | | |
|---|---|---|---|---|
| tgcaccgcca | gccagaagaa | gtccatccag | ttccactgga | agaacagcaa ccagatcaag | 180 |
| atcctgggca | accagggcag | cttcctgacc | aagggcccca | gcaagctgaa cgaccgggcc | 240 |
| gatagccggc | ggagcctgtg | ggaccagggc | aatttcccac | tgatcatcaa gaacctgaag | 300 |
| atcgaggaca | gcgacaccta | catctgcgag | gtcgaagatc | agaaagaaga ggtgcagctg | 360 |
| ctggtgttcg | gcctgaccgc | caactccgac | acccatctgc | tgcagggcca gagcctgacc | 420 |
| ctcaccctgg | aaagcccccc | tggcagcagc | cccagcgtgc | agtgcagaag ccccagaggc | 480 |
| aagaacatcc | agggcggcaa | gaccctgagc | gtgtcccagc | tggaactgca ggactccggc | 540 |
| acctggacct | gtaccgtgct | gcagaaccag | aaaaaggtcg | agttcaagat cgacatcgtg | 600 |
| gtgctggcct | tccagaaggc | cctggcggcc | ggaggatctg | gcggaggtgg aagtggcggg | 660 |
| ggaggtagtg | gcggaggcgg | atcaggtggc | ggaggttcag | gcggtggcgg aagcggaggc | 720 |
| ggtggatctc | aggtccagct | gctcgaatct | ggcgccgaag | tgaagaaacc cggcagcagc | 780 |
| gtgaaagtgt | cctgcaaggc | cagcggcgac | accttcatcc | ggtacagctt cacatgggtc | 840 |
| cgacaggccc | ctgggcaggg | cctggaatgg | atgggccgga | tcatcaccat cctggacgtg | 900 |
| gcccactacg | ccccacatct | gcagggcaga | gtgaccatca | ccgccgacaa gagcaccagc | 960 |
| accgtgtacc | tggaactgcg | gaacctgcgg | agcgacgata | ccgccgtcta cttctgtgcc | 1020 |
| ggcgtgtacg | agggcgaggc | cgatgagggc | gagtacgaca | caacggcttc ctgaagcac | 1080 |
| tggggccagg | gcaccctcgt | caccgtgacc | agcgcggcg | gaggatctgg cggaggtgga | 1140 |
| agtggcgggg | gaggtagtga | gctggaactc | acccagagcc | ccgccaccct gtccgtgtct | 1200 |
| ccaggcgaga | gagccaccct | gagctgcaga | gccagcgaga | gcgtgtccag cgacctggcc | 1260 |
| tggtatcagc | agaagcccgg | ccaggccccc | agactgctga | tctacggcgc cagcaccaga | 1320 |
| gccacaggcg | tgccagccag | attcagcggc | agcggtagcg | gagccgagtt caccctgacc | 1380 |
| atcagcagcc | tgcagagcga | ggactttgcc | gtgtactact | gccagcagta caacaactgg | 1440 |
| ccccccagat | acaccttcgg | ccagggaacc | cggctggaaa | tcaaggcggc cgcaattgaa | 1500 |
| gttatgtatc | ctcctccta | cctagacaat | gagaagagca | atggaaccat tatccatgtg | 1560 |
| aaagggaaac | acctttgtcc | aagtccccta | tttcccggac | cttctaagcc cttttgggtg | 1620 |
| ctggtggtgg | ttggtggagt | cctggcttgc | tatagcttgc | tagtaacagt ggcctttatt | 1680 |
| attttctggg | tgaggagtaa | gaggagcagg | ctcctgcaca | gtgactacat gaacatgact | 1740 |
| ccccgccgcc | ccgggcccac | ccgcaagcat | taccagcct | atgccccacc acgcgacttc | 1800 |
| gcagcctatc | gctccagagt | gaagttcagc | aggagcgcag | acgccccgc gtaccagcag | 1860 |
| ggccagaacc | agctctataa | cgagctcaat | ctaggacgaa | gagaggagta cgatgttttg | 1920 |
| gacaagagac | gtggccggga | ccctgagatg | ggggaaagc | cgagaaggaa gaaccctcag | 1980 |
| gaaggcctgt | acaatgaact | gcagaaagat | aagatggcgg | aggcctacag tgagattggg | 2040 |
| atgaaaggcg | agcgccggag | gggcaagggg | cacgatggcc | tttaccaggg tctcagtaca | 2100 |
| gccaccaagg | acacctacga | cgcccttcac | atgcaggccc | tgcccctcg ctaa | 2154 |

<210> SEQ ID NO 8
<211> LENGTH: 692
<212> TYPE: PRT
<213> ORGANISM: Artificial Sequence
<220> FEATURE:
<223> OTHER INFORMATION: Protein encoded by synthetically generated
      expression cassette

<400> SEQUENCE: 8

-continued

```
Met Val Arg Gly Val Pro Phe Arg His Leu Leu Val Leu Gln Leu
1               5                   10                  15

Ala Leu Leu Pro Ala Ala Thr Gln Gly Lys Lys Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
            130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Phe Gln Lys Ala Ser
            195                 200                 205

Gly Gly Gly Gly Ser Gly Gly Gly Ser Gln Val Gln Leu Leu Glu
210                 215                 220

Ser Gly Ala Glu Val Lys Lys Pro Gly Ser Ser Val Lys Val Ser Cys
225                 230                 235                 240

Lys Ala Ser Gly Asp Thr Phe Ile Arg Tyr Ser Phe Thr Trp Val Arg
                245                 250                 255

Gln Ala Pro Gly Gln Gly Leu Glu Trp Met Gly Arg Ile Ile Thr Ile
            260                 265                 270

Leu Asp Val Ala His Tyr Ala Pro His Leu Gln Gly Arg Val Thr Ile
            275                 280                 285

Thr Ala Asp Lys Ser Thr Ser Thr Val Tyr Leu Glu Leu Arg Asn Leu
290                 295                 300

Arg Ser Asp Asp Thr Ala Val Tyr Phe Cys Ala Gly Val Tyr Glu Gly
305                 310                 315                 320

Glu Ala Asp Glu Gly Glu Tyr Asp Asn Asn Gly Phe Leu Lys His Trp
            325                 330                 335

Gly Gln Gly Thr Leu Val Thr Val Thr Ser Gly Gly Gly Gly Ser Gly
            340                 345                 350

Gly Gly Gly Ser Gly Gly Gly Gly Ser Glu Leu Glu Leu Thr Gln Ser
            355                 360                 365

Pro Ala Thr Leu Ser Val Ser Pro Gly Glu Arg Ala Thr Leu Ser Cys
            370                 375                 380

Arg Ala Ser Glu Ser Val Ser Ser Asp Leu Ala Trp Tyr Gln Gln Lys
385                 390                 395                 400

Pro Gly Gln Ala Pro Arg Leu Leu Ile Tyr Gly Ala Ser Thr Arg Ala
                405                 410                 415
```

-continued

```
Thr Gly Val Pro Ala Arg Phe Ser Gly Ser Gly Ser Gly Ala Glu Phe
                420                 425                 430
Thr Leu Thr Ile Ser Ser Leu Gln Ser Glu Asp Phe Ala Val Tyr Tyr
            435                 440                 445
Cys Gln Gln Tyr Asn Asn Trp Pro Pro Arg Tyr Thr Phe Gly Gln Gly
        450                 455                 460
Thr Arg Leu Glu Ile Lys Ala Ala Ile Glu Val Met Tyr Pro Pro
465                 470                 475                 480
Pro Tyr Leu Asp Asn Glu Lys Ser Asn Gly Thr Ile Ile His Val Lys
                485                 490                 495
Gly Lys His Leu Cys Pro Ser Pro Leu Phe Pro Gly Pro Ser Lys Pro
            500                 505                 510
Phe Trp Val Leu Val Val Val Gly Gly Val Leu Ala Cys Tyr Ser Leu
        515                 520                 525
Leu Val Thr Val Ala Phe Ile Ile Phe Trp Val Arg Ser Lys Arg Ser
    530                 535                 540
Arg Leu Leu His Ser Asp Tyr Met Asn Met Thr Pro Arg Arg Pro Gly
545                 550                 555                 560
Pro Thr Arg Lys His Tyr Gln Pro Tyr Ala Pro Pro Arg Asp Phe Ala
                565                 570                 575
Ala Tyr Arg Ser Arg Val Lys Phe Ser Arg Ser Ala Asp Ala Pro Ala
            580                 585                 590
Tyr Gln Gln Gly Gln Asn Gln Leu Tyr Asn Glu Leu Asn Leu Gly Arg
        595                 600                 605
Arg Glu Glu Tyr Asp Val Leu Asp Lys Arg Arg Gly Arg Asp Pro Glu
    610                 615                 620
Met Gly Gly Lys Pro Arg Arg Lys Asn Pro Gln Glu Gly Leu Tyr Asn
625                 630                 635                 640
Glu Leu Gln Lys Asp Lys Met Ala Glu Ala Tyr Ser Glu Ile Gly Met
                645                 650                 655
Lys Gly Glu Arg Arg Arg Gly Lys Gly His Asp Gly Leu Tyr Gln Gly
            660                 665                 670
Leu Ser Thr Ala Thr Lys Asp Thr Tyr Asp Ala Leu His Met Gln Ala
        675                 680                 685
Leu Pro Pro Arg
    690
```

```
<210> SEQ ID NO 9
<211> LENGTH: 2079
<212> TYPE: DNA
<213> ORGANISM: Artificial Sequence
<220> FEATURE:
<223> OTHER INFORMATION: Synthetically generated expression cassette

<400> SEQUENCE: 9
atggttcgag gcgtgccctt ccggcatctg ctgctggtgc tgcagctggc tctcctgcct    60
gccgccaccc agggcaagaa agtggtgctg ggcaaaaagg cgacaccgt ggaactgacc     120 tgcaccgcca gccagaagaa gtccatccag ttccactgga agaacagcaa ccagatcaag    180
atcctgggca accagggcag cttcctgacc aagggcccca gcaagctgaa cgaccgggcc    240
gatagccggc ggagcctgtg ggaccagggc aatttcccac tgatcatcaa gaacctgaag    300
atcgaggaca cgacacccta catctgcgag gtcgaagatc agaaagaaga ggtgcagctg    360
ctggtgttcg gcctgaccgc caactccgac acccatctgc tgcagggcca gagcctgacc    420
ctcaccctgg aaagccccc tgcagcagc ccagcgtgc agtgcagaag ccccagaggc    480
```

```
aagaacatcc agggcggcaa gaccctgagc gtgtcccagc tggaactgca ggactccggc    540
acctggacct gtaccgtgct gcagaaccag aaaaaggtcg agttcaagat cgacatcgtg    600
gtgctggcct tccagaaggc ctctggcggt ggcggaagcg gaggcggtgg atctcaggtc    660
cagctgctcg aatctggcgc cgaagtgaag aaacccggca gcagcgtgaa agtgtcctgc    720
aaggccagcg gcgacacctt catccggtac agcttcacat gggtccgaca ggcccctggg    780
cagggcctgg aatggatggg ccggatcatc accatcctgg acgtggccca ctacgcccca    840
catctgcagg gcagagtgac catcaccgcc gacaagagca ccagcaccgt gtacctggaa    900
ctgcggaacc tgcggagcga cgataccgcc gtctacttct gtgccggcgt gtacgagggc    960
gaggccgatg agggcgagta cgacaacaac ggcttcctga agcactgggg ccagggcacc   1020
ctcgtcaccg tgaccagcgg cggcggagga tctggcggag gtggaagtgg cggggggaggt   1080 agtgagctgg aactcaccca gagccccgcc accctgtccg tgtctccagg cgagagagcc   1140
accctgagct gcagagccag cgagagcgtg tccagcgacc tggcctggta tcagcagaag   1200
cccggccagg cccccagact gctgatctac ggcgccagca ccagagccac aggcgtgcca   1260
gccagattca gcggcagcgg tagcggagcc gagttcaccc tgaccatcag cagcctgcag   1320
agcgaggact ttgccgtgta ctactgccag cagtacaaca ctggccccc  cagatacacc   1380 ttcggccagg gaacccggct ggaaatcaag gcggccgcaa ttgaagttat gtatcctcct   1440
ccttacctag acaatgagaa gagcaatgga accattatcc atgtgaaagg gaaacacctt   1500
tgtccaagtc ccctatttcc cggaccttct aagccctttt gggtgctggt ggtggttggt   1560
ggagtcctgg cttgctatag cttgctagta acagtggcct ttattatttt ctgggtgagg   1620
agtaagagga gcaggctcct gcacagtgac tacatgaaca tgactccccg ccgcccggg    1680 cccacccgca agcattacca gccctatgcc ccaccacgcg acttcgcagc ctatcgctcc   1740
agagtgaagt tcagcaggag cgcagacgcc cccgcgtacc agcagggcca gaaccagctc   1800
tataacgagc tcaatctagg acgaagagag gagtacgatg ttttggacaa gagacgtggc   1860
cgggaccctg agatgggggg aaagccgaga aggaagaacc ctcaggaagg cctgtacaat   1920
gaactgcaga aagataagat ggcggaggcc tacagtgaga ttgggatgaa aggcgagcgc   1980 cggagggggca aggggcacga tggcctttac cagggtctca gtacagccac caaggacacc   2040
tacgacgccc ttcacatgca ggccctgccc cctcgctaa                          2079
```

<210> SEQ ID NO 10
<211> LENGTH: 708
<212> TYPE: PRT
<213> ORGANISM: Artificial Sequence
<220> FEATURE:
<223> OTHER INFORMATION: Protein encoded by synthetically generated
     expression cassette

<400> SEQUENCE: 10

Met Val Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala

-continued

```
                65                  70                  75                  80
Asp Ser Arg Arg Ser Leu Trp Asp Gln Gly Asn Phe Pro Leu Ile Ile
                    85                  90                  95
Lys Asn Leu Lys Ile Glu Asp Ser Asp Thr Tyr Ile Cys Glu Val Glu
                    100                 105                 110
Asp Gln Lys Glu Glu Val Gln Leu Leu Val Phe Gly Leu Thr Ala Asn
                    115                 120                 125
Ser Asp Thr His Leu Leu Gln Gly Gln Ser Leu Thr Leu Thr Leu Glu
            130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                    165                 170                 175
Gln Asp Ser Gly Thr Trp Thr Cys Thr Val Leu Gln Asn Gln Lys Lys
                    180                 185                 190
Val Glu Phe Lys Ile Asp Ile Val Val Leu Ala Phe Gln Lys Ala Ser
                    195                 200                 205
Gly Gly Gly Gly Ser Gly Gly Gly Ser Gly Gly Gly Gly Ser Gly
            210                 215                 220
Gly Gly Gly Ser Gly Gly Gly Ser Gly Gly Gly Ser Gly Gly
225                 230                 235                 240
Gly Gly Ser Glu Val Gln Leu Val Gln Ser Gly Ala Glu Val Lys Lys
                    245                 250                 255
Pro Gly Ala Thr Val Lys Ile Ser Cys Lys Val Ser Gly Tyr Thr Phe
                    260                 265                 270
Thr Asp Tyr Tyr Met His Trp Val Gln Gln Ala Pro Gly Lys Gly Leu
                    275                 280                 285
Glu Trp Met Gly Leu Val Asp Pro Glu Asp Gly Glu Thr Ile Tyr Ala
            290                 295                 300
Glu Lys Phe Gln Gly Arg Val Thr Ile Thr Ala Asp Thr Ser Thr Asp
305                 310                 315                 320
Thr Ala Tyr Met Glu Leu Ser Ser Leu Arg Ser Glu Asp Thr Ala Val
                    325                 330                 335
Tyr Tyr Cys Ala Thr Glu Arg Thr Asp Tyr Trp Gly Gln Gly Thr Leu
                    340                 345                 350
Val Thr Val Ser Ser Gly Gly Gly Gly Ser Gly Gly Gly Gly Ser Gly
                    355                 360                 365
Gly Gly Gly Ser Glu Ile Val Leu Thr Gln Ser Pro Leu Ser Leu Ser
            370                 375                 380
Val Thr Pro Gly Glu Pro Ala Ser Ile Ser Cys Arg Ser Ser Gln Ser
385                 390                 395                 400
Leu Leu Asp Ser Asp Asp Gly Asn Thr Tyr Leu Asp Trp Tyr Leu Gln
                    405                 410                 415
Lys Pro Gly Gln Ser Pro Gln Leu Leu Ile Tyr Glu Val Ser Asn Arg
                    420                 425                 430
Phe Ser Gly Val Pro Asp Arg Phe Ser Gly Ser Gly Ser Gly Thr Asp
                    435                 440                 445
Phe Thr Leu Lys Ile Ser Arg Val Glu Ala Glu Asp Val Gly Val Tyr
                    450                 455                 460
Tyr Cys Met Gln Ser Ile Gln Leu Pro Trp Thr Phe Gly Gln Gly Thr
465                 470                 475                 480
Lys Leu Glu Ile Lys Arg Ala Ala Ala Ile Glu Val Met Tyr Pro Pro
                    485                 490                 495
```

```
Pro Tyr Leu Asp Asn Glu Lys Ser Asn Gly Thr Ile Ile His Val Lys
            500                 505                 510
Gly Lys His Leu Cys Pro Ser Pro Leu Phe Pro Gly Pro Ser Lys Pro
            515                 520                 525
Phe Trp Val Leu Val Val Gly Gly Val Leu Ala Cys Tyr Ser Leu
        530                 535                 540
Leu Val Thr Val Ala Phe Ile Ile Phe Trp Val Arg Ser Lys Arg Ser
545                 550                 555                 560
Arg Leu Leu His Ser Asp Tyr Met Asn Met Thr Pro Arg Arg Pro Gly
                565                 570                 575
Pro Thr Arg Lys His Tyr Gln Pro Tyr Ala Pro Pro Arg Asp Phe Ala
            580                 585                 590
Ala Tyr Arg Ser Arg Val Lys Phe Ser Arg Ser Ala Asp Ala Pro Ala
        595                 600                 605
Tyr Gln Gln Gly Gln Asn Gln Leu Tyr Asn Glu Leu Asn Leu Gly Arg
610                 615                 620
Arg Glu Glu Tyr Asp Val Leu Asp Lys Arg Gly Arg Asp Pro Glu
625                 630                 635                 640
Met Gly Gly Lys Pro Arg Arg Lys Asn Pro Gln Glu Gly Leu Tyr Asn
                645                 650                 655
Glu Leu Gln Lys Asp Lys Met Ala Glu Ala Tyr Ser Glu Ile Gly Met
            660                 665                 670
Lys Gly Glu Arg Arg Arg Gly Lys Gly His Asp Gly Leu Tyr Gln Gly
        675                 680                 685
Leu Ser Thr Ala Thr Lys Asp Thr Tyr Asp Ala Leu His Met Gln Ala
    690                 695                 700
Leu Pro Pro Arg
705

<210> SEQ ID NO 11
<211> LENGTH: 2127
<212> TYPE: DNA
<213> ORGANISM: Artificial Sequence
<220> FEATURE:
<223> OTHER INFORMATION: Synthetically generated expression cassette

<400> SEQUENCE: 11
atggttcgag gcgtgccctt ccggcatctg ctgctggtgc tgcagctggc tctcctgcct      60
gccgccaccc agggcaagaa agtggtgctg ggcaaaaagg cgacaccgt ggaactgacc      120 tgcaccgcca gccagaagaa gtccatccag ttccactgga agaacagcaa ccagatcaag      180
atcctgggca accagggcag cttcctgacc aagggcccca gcaagctgaa cgaccgggcc      240
gatagccggc ggagcctgtg ggaccagggc aatttcccac tgatcatcaa gaacctgaag      300
atcgaggaca gcgacaccta catctgcgag gtcgaagatc agaaagaaga ggtgcagctg      360
ctggtgttcg gcctgaccgc caactccgac acccatctgc tgcagggcca gagcctgacc      420
ctcacccctg gaaagccccc tggcagcagc cccagcgtgc agtgcagaag ccccagaggc      480
aagaacatcc agggcggcaa gaccctgagc gtgtcccagc tggaactgca ggactccggc      540
acctggacct gtaccgtgct gcagaaccag aaaaaggtcg agttcaagat cgacatcgtg      600
gtgctggcct tccagaaggc ctctggcggc ggaggatctg gcggaggtgg aagtggcggg      660
ggaggtagtg gcggaggcgg atcaggtggc ggaggttcag gcggtggcgg aagcggaggc      720
ggtggatctg aagtgcagct ggtgcagtct ggcgccgaag tgaagaaacc tggcgccacc      780
```

-continued

```
gtgaagatca gctgcaaggt gtccggctac accttcaccg actactacat gcactgggtg    840
cagcaggccc ctggcaaggg cctggaatgg atgggactgg tggaccccga ggacggcgag    900
acaatctacg ccgagaagtt ccagggcaga gtgaccatca ccgccgatac cagcaccgac    960
accgcctaca tggaactgag cagcctgcgg agcgaggaca ccgccgtgta ctactgtgcc   1020
accgagcgga ccgattactg gggccaggga acactcgtga ccgtgtcaag tggcggcgga   1080
ggatctggcg gaggtggaag tggcgggggga ggtagtgaga tcgtgctgac ccagagcccc   1140
ctgtccctgt ctgtgacacc tggcgagcct gccagcatct cctgcagaag cagccagagc   1200
ctgctggact ccgacgacgg caacacctac ctggactggt atctgcagaa acccggccag   1260
tccccccagc tgctgatcta cgaggtgtcc aaccggttca gcggcgtgcc cgatagattt   1320
tccggctctg gcagcggcac cgacttcacc ctgaagatta gccgggtgga agccgaggac   1380
gtgggcgtgt actattgcat gcagagcatc cagctgcctt ggaccttcgg ccagggcacc   1440
aagctggaaa tcaagagagc ggccgcaatt gaagttatgt atcctcctcc ttacctagac   1500
aatgagaaga gcaatggaac cattatccat gtgaaaggga aacacctttg tccaagtccc   1560
ctatttcccg gaccttctaa gcccttttgg gtgctggtgg tggttggtgg agtcctggct   1620
tgctatagct tgctagtaac agtggccttt attattttct gggtgaggag taagaggagc   1680
aggctcctgc acagtgacta catgaacatg actccccgcc gccccgggcc cacccgcaag   1740
cattaccagc cctatgcccc accacgcgac ttcgcagcct atcgctccag agtgaagttc   1800
agcaggagcg cagacgcccc cgcgtaccag cagggccaga accagctcta taacgagctc   1860
aatctaggac gaagagagga gtacgatgtt ttggacaaga gacgtggccg ggaccctgag   1920
atgggggggaa agccgagaag gaagaaccct caggaaggcc tgtacaatga actgcagaaa   1980
gataagatgg cggaggccta cagtgagatt gggatgaaag gcgagcgccg gaggggcaag   2040
gggcacgatg gcctttacca gggtctcagt acagccacca aggacaccta cgacgccctt   2100
cacatgcagg ccctgccccc tcgctaa                                       2127
```